United States Patent
Svarovsky et al.

(10) Patent No.: US 11,789,020 B2
(45) Date of Patent: Oct. 17, 2023

(54) NEUTRALIZING ANTIBODY TESTING AND TREATMENT

(71) Applicants: Sapphire Biotech, Inc., San Diego, CA (US); ARIZONA BOARD OF REGENTS ON BEHALF OF ARIZONA STATE UNIVERSITY, Scottsdale, AZ (US)

(72) Inventors: Sergei Svarovsky, San Diego, CA (US); Douglas Lake, Scottsdale, AZ (US); Alim Seit-Nebi, San Diego, CA (US); María González-Moa, San Diego, CA (US)

(73) Assignee: Sapphire Biotech, Inc., San Diego, CA (US)

( * ) Notice: Subject to any disclaimer, the term of this patent is extended or adjusted under 35 U.S.C. 154(b) by 128 days.

(21) Appl. No.: 17/319,081

(22) Filed: May 12, 2021

(65) Prior Publication Data

US 2021/0356465 A1    Nov. 18, 2021

Related U.S. Application Data

(60) Provisional application No. 63/023,646, filed on May 12, 2020, provisional application No. 63/116,749, filed on Nov. 20, 2020.

(51) Int. Cl.
*G01N 33/569* (2006.01)
*G01N 33/543* (2006.01)

(52) U.S. Cl.
CPC ......... *G01N 33/56983* (2013.01); *G01N 33/54346* (2013.01); *G01N 33/54388* (2021.08); *G01N 2333/165* (2013.01); *G01N 2469/20* (2013.01); *G01N 2800/26* (2013.01)

(58) Field of Classification Search
None
See application file for complete search history.

(56) References Cited

U.S. PATENT DOCUMENTS

| | | | |
|---|---|---|---|
| 2005/0249739 A1 | 11/2005 | Marasco et al. | |
| 2006/0292162 A1 | 12/2006 | Buckheit et al. | |
| 2013/0224771 A1* | 8/2013 | McDade | G01N 33/74 435/7.1 |
| 2014/0377770 A1* | 12/2014 | Bischof | G01N 25/4806 435/7.1 |
| 2021/0311052 A1* | 10/2021 | Lapointe | G01N 33/54366 |

FOREIGN PATENT DOCUMENTS

WO    2005027963 A2    3/2005

OTHER PUBLICATIONS

International Search Report and Written Opinion for PCT/US2021/032106 dated Sep. 16, 2021; 11 pages.
Okba et al., "SARS-CoV-2 specific antibody responses in COVID-19 patients," medRxiv, Mar. 20, 2020, pp. 1-18.
Mcaulay et al., "Retrospective clinical evaluation of 4 lateral flow assays for the detection of SARS-COV-2 IgG," Virology, Aug. 2, 2020, vol. 98, Iss. 3, pp. 206.

* cited by examiner

*Primary Examiner* — Nianxiang Zou
(74) *Attorney, Agent, or Firm* — Procopio, Cory, Hargreaves & Savitch LLP

(57) ABSTRACT

Provided herein are diagnostic methods, devices and kits for detecting neutralizing antibodies to SARS-CoV-2.

54 Claims, 16 Drawing Sheets
Specification includes a Sequence Listing.

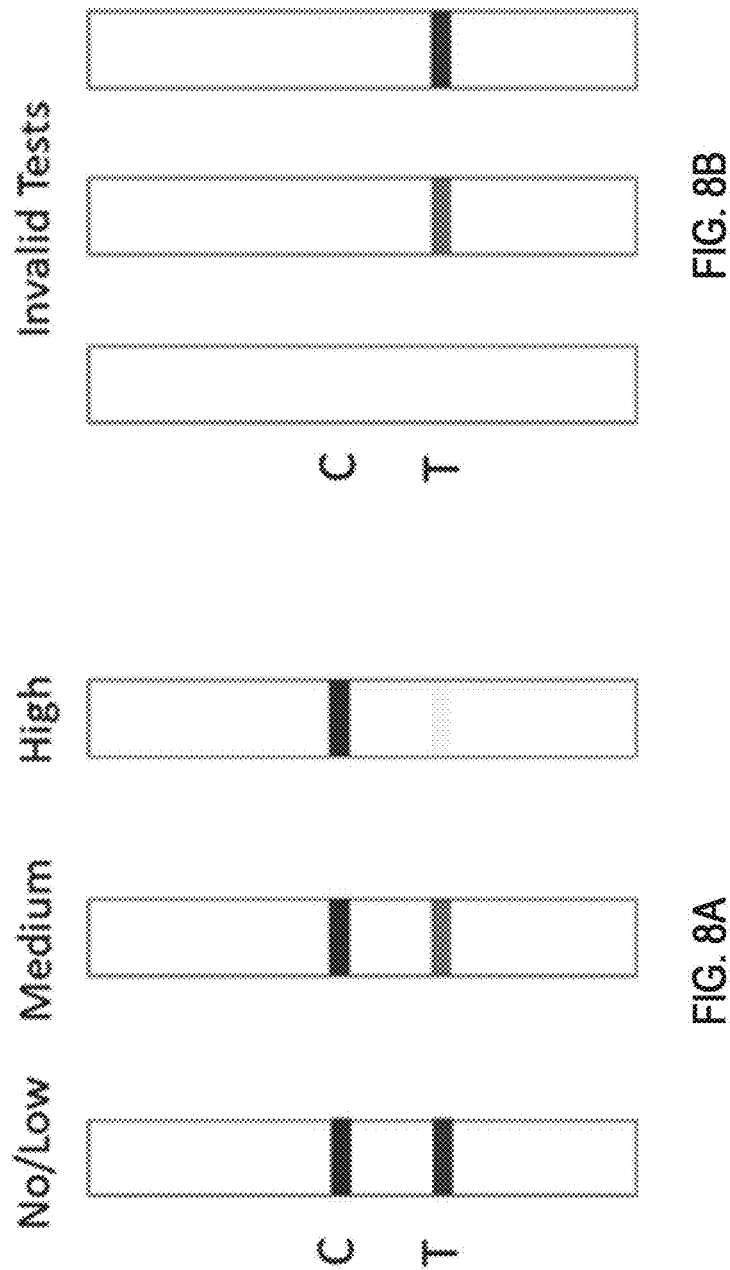

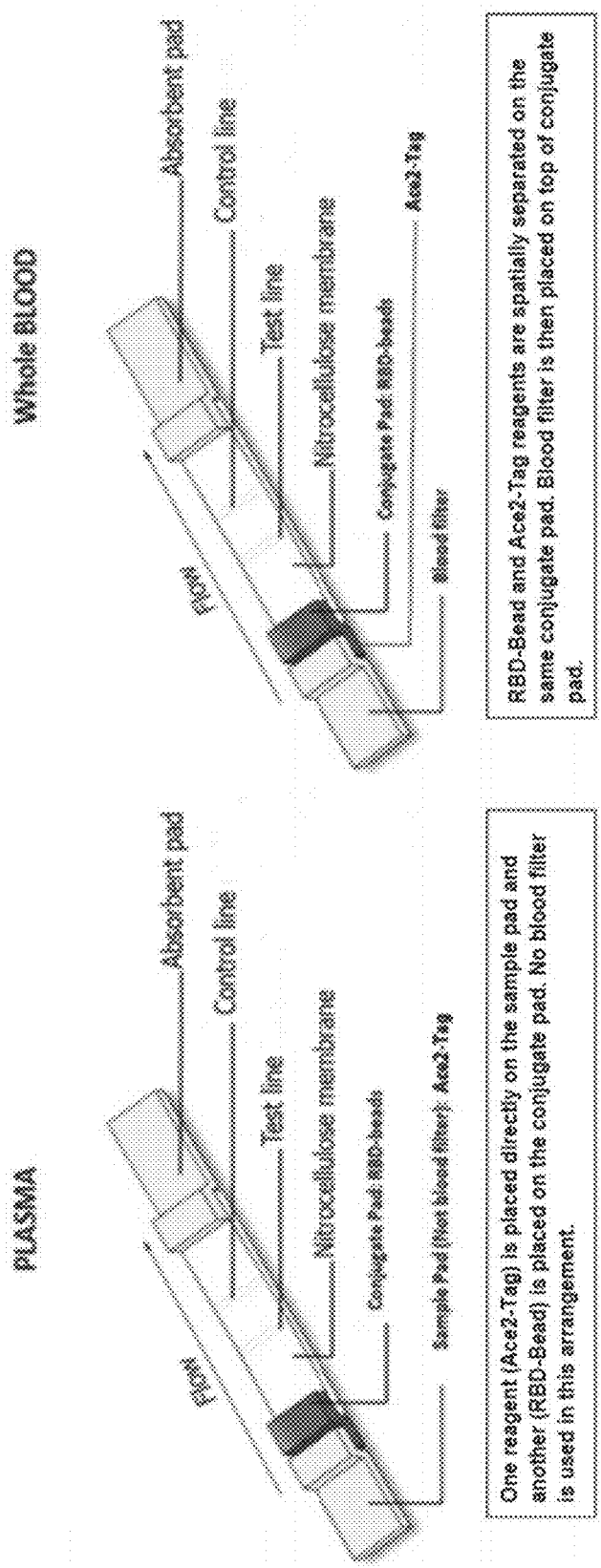

SEQUENCE LISTING

```
<160> NUMBER OF SEQ ID NOS: 3

<210> SEQ ID NO 1
<211> LENGTH: 272
<212> TYPE: PRT
<213> ORGANISM: Unknown
<220> FEATURE:
<223> OTHER INFORMATION: Description of Unknown:
      SARS-CoV-2 spike protein

<400> SEQUENCE: 1

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Pro Thr Asn Gly Val Gly Tyr Gln Pro Tyr Arg Val Val
            180                 185                 190

Val Leu Ser Phe Glu Leu Leu His Ala Pro Ala Thr Val Cys Gly Pro
        195                 200                 205
```

Lys Lys Ser Thr Asn Leu Val Lys Asn Lys Cys Val Asn Phe Asn Phe
            210                 215                 220

Asn Gly Leu Thr Gly Thr Gly Val Leu Thr Glu Ser Asn Lys Lys Phe
225                 230                 235                 240

Leu Pro Phe Gln Gln Phe Gly Arg Asp Ile Ala Asp Thr Thr Asp Ala
                245                 250                 255

Val Arg Asp Pro Gln Thr Leu Glu Ile Leu Asp Ile Thr Pro Cys Ser
            260                 265                 270

<210> SEQ ID NO 2
<211> LENGTH: 224
<212> TYPE: PRT
<213> ORGANISM: Unknown
<220> FEATURE:
<223> OTHER INFORMATION: Description of Unknown:
      SARS-CoV-2 spike protein

<400> SEQUENCE: 2

Gln Arg Val Gln Pro Thr Glu Ser Ile Val Arg Phe Pro Asn Ile Thr
1               5                   10                  15

Asn Leu Cys Pro Phe Gly Glu Val Phe Asn Ala Thr Arg Phe Ala Ser
            20                  25                  30

Val Tyr Ala Trp Asn Arg Lys Arg Ile Ser Asn Cys Val Ala Asp Tyr
        35                  40                  45

Ser Val Leu Tyr Asn Ser Ala Ser Phe Ser Thr Phe Lys Cys Tyr Gly
    50                  55                  60

Val Ser Pro Thr Lys Leu Asn Asp Leu Cys Phe Thr Asn Val Tyr Ala
65                  70                  75                  80

Asp Ser Phe Val Ile Arg Gly Asp Glu Val Arg Gln Ile Ala Pro Gly
                85                  90                  95

Gln Thr Gly Lys Ile Ala Asp Tyr Asn Tyr Lys Leu Pro Asp Asp Phe
            100                 105                 110

Thr Gly Cys Val Ile Ala Trp Asn Ser Asn Asn Leu Asp Ser Lys Val
        115                 120                 125

Gly Gly Asn Tyr Asn Tyr Leu Tyr Arg Leu Phe Arg Lys Ser Asn Leu
    130                 135                 140

Lys Pro Phe Glu Arg Asp Ile Ser Thr Glu Ile Tyr Gln Ala Gly Ser
145                 150                 155                 160

Thr Pro Cys Asn Gly Val Glu Gly Phe Asn Cys Tyr Phe Pro Leu Gln
                165                 170                 175

Ser Tyr Gly Phe Gln Pro Thr Asn Gly Val Gly Tyr Gln Pro Tyr Arg
            180                 185                 190

Val Val Val Leu Ser Phe Glu Leu Leu His Ala Pro Ala Thr Val Cys
        195                 200                 205

Gly Pro Lys Lys Ser Thr Asn Leu Val Lys Asn Lys Cys Val Asn Phe
    210                 215                 220

<210> SEQ ID NO 3
<211> LENGTH: 598
<212> TYPE: PRT
<213> ORGANISM: Homo sapiens

<400> SEQUENCE: 3

Gln Ser Thr Ile Glu Glu Gln Ala Lys Thr Phe Leu Asp Lys Phe Asn
1               5                   10                  15

His Glu Ala Glu Asp Leu Phe Tyr Gln Ser Ser Leu Ala Ser Trp Asn
            20                  25                  30

```
Tyr Asn Thr Asn Ile Thr Glu Glu Asn Val Gln Asn Met Asn Asn Ala
         35                  40                  45
Gly Asp Lys Trp Ser Ala Phe Leu Lys Glu Gln Ser Thr Leu Ala Gln
 50                  55                  60
Met Tyr Pro Leu Gln Glu Ile Gln Asn Leu Thr Val Lys Leu Gln Leu
 65                  70                  75                  80
Gln Ala Leu Gln Gln Asn Gly Ser Ser Val Leu Ser Glu Asp Lys Ser
                 85                  90                  95
Lys Arg Leu Asn Thr Ile Leu Asn Thr Met Ser Thr Ile Tyr Ser Thr
                100                 105                 110
Gly Lys Val Cys Asn Pro Asp Asn Pro Gln Cys Leu Leu Leu Glu
                115                 120                 125
Pro Gly Leu Asn Glu Ile Met Ala Asn Ser Leu Asp Tyr Asn Glu Arg
130                 135                 140
Leu Trp Ala Trp Glu Ser Trp Arg Ser Glu Val Gly Lys Gln Leu Arg
145                 150                 155                 160
Pro Leu Tyr Glu Glu Tyr Val Val Leu Lys Asn Glu Met Ala Arg Ala
                165                 170                 175
Asn His Tyr Glu Asp Tyr Gly Asp Tyr Trp Arg Gly Asp Tyr Glu Val
                180                 185                 190
Asn Gly Val Asp Gly Tyr Asp Tyr Ser Arg Gly Gln Leu Ile Glu Asp
                195                 200                 205
Val Glu His Thr Phe Glu Glu Ile Lys Pro Leu Tyr Glu His Leu His
210                 215                 220
Ala Tyr Val Arg Ala Lys Leu Met Asn Ala Tyr Pro Ser Tyr Ile Ser
225                 230                 235                 240
Pro Ile Gly Cys Leu Pro Ala His Leu Leu Gly Asp Met Trp Gly Arg
                245                 250                 255
Phe Trp Thr Asn Leu Tyr Ser Leu Thr Val Pro Phe Gly Gln Lys Pro
                260                 265                 270
Asn Ile Asp Val Thr Asp Ala Met Val Asp Gln Ala Trp Asp Ala Gln
                275                 280                 285
Arg Ile Phe Lys Glu Ala Glu Lys Phe Phe Val Ser Val Gly Leu Pro
290                 295                 300
Asn Met Thr Gln Gly Phe Trp Glu Asn Ser Met Leu Thr Asp Pro Gly
305                 310                 315                 320
Asn Val Gln Lys Ala Val Cys His Pro Thr Ala Trp Asp Leu Gly Lys
                325                 330                 335
Gly Asp Phe Arg Ile Leu Met Cys Thr Lys Val Thr Met Asp Asp Phe
                340                 345                 350
Leu Thr Ala His His Glu Met Gly His Ile Gln Tyr Asp Met Ala Tyr
                355                 360                 365
Ala Ala Gln Pro Phe Leu Leu Arg Asn Gly Ala Asn Glu Gly Phe His
370                 375                 380
Glu Ala Val Gly Glu Ile Met Ser Leu Ser Ala Ala Thr Pro Lys His
385                 390                 395                 400
Leu Lys Ser Ile Gly Leu Leu Ser Pro Asp Phe Gln Glu Asp Asn Glu
                405                 410                 415
Thr Glu Ile Asn Phe Leu Leu Lys Gln Ala Leu Thr Ile Val Gly Thr
                420                 425                 430
Leu Pro Phe Thr Tyr Met Leu Glu Lys Trp Arg Trp Met Val Phe Lys
                435                 440                 445
```

-continued

```
Gly Glu Ile Pro Lys Asp Gln Trp Met Lys Lys Trp Trp Glu Met Lys
    450                 455                 460
Arg Glu Ile Val Gly Val Val Glu Pro Val Pro His Asp Glu Thr Tyr
465                 470                 475                 480
Cys Asp Pro Ala Ser Leu Phe His Val Ser Asn Asp Tyr Ser Phe Ile
                485                 490                 495
Arg Tyr Tyr Thr Arg Thr Leu Tyr Gln Phe Gln Phe Gln Glu Ala Leu
            500                 505                 510
Cys Gln Ala Ala Lys His Glu Gly Pro Leu His Lys Cys Asp Ile Ser
        515                 520                 525
Asn Ser Thr Glu Ala Gly Gln Lys Leu Phe Asn Met Leu Arg Leu Gly
    530                 535                 540
Lys Ser Glu Pro Trp Thr Leu Ala Leu Glu Asn Val Val Gly Ala Lys
545                 550                 555                 560
Asn Met Asn Val Arg Pro Leu Leu Asn Tyr Phe Glu Pro Leu Phe Thr
                565                 570                 575
Trp Leu Lys Asp Gln Asn Lys Asn Ser Phe Val Gly Trp Ser Thr Asp
            580                 585                 590
Trp Ser Pro Tyr Ala Asp
        595
```

NEUTRALIZING ANTIBODY TESTING AND TREATMENT

CROSS-REFERENCE TO RELATED APPLICATIONS

This application claims priority to U.S. Provisional Application No. 63/023,646, filed May 12, 2020 and U.S. Provisional Application No. 63/116,749, filed on Nov. 20, 2020, the contents of which are incorporated by herein by reference.

The invention relates to diagnostic methods, devices and kits for detecting neutralizing antibodies to SARS-CoV-2.

BACKGROUND

SARS-CoV-2 is a β coronavirus and causes COVID-19, an acute respiratory infectious disease. Humans are generally susceptible. Individuals infected with SARS-CoV-2 are the main source of infection, but infected people who are asymptomatically infected are also a source of infection. Based on the current epidemiological investigation, the incubation period is 2 to 14 days, with a median of 5 days. The main manifestations of COVID19 include fever, fatigue and dry cough. Nasal congestion, runny nose, sore throat, myalgia and diarrhea may also be present.

People who've recovered from COVID-19 have antibodies to the virus in their blood. Plasma prepared from these individuals is referred to as COVID19 convalescent plasma (CCP). CCP can be given to people with severe COVID-19 with the intention of boosting their ability to fight the virus.

Once someone recovers clinically and tests: (A) negative by PCR (no live virus present) and (B) positive by serology test (antibodies to SARS-Cov2 present), they may be asked if they would like to donate CCP. If they agree, they undergo plasmapheresis after which their plasma is then frozen, usually in 200 cc units.

When someone fighting COVID19 needs CCP, a unit of frozen plasma is available. No tests for antibody abundance or their ability to neutralize the virus are performed. It is assumed that CCP contains neutralizing antibodies.

However, it has been shown that some patients make high titers of neutralizing Ab, but others don't at all—even though they both recover. This means some patients get much more neutralizing Ab than they need while others don't get enough.

Because it is of high clinical interest to correlate neutralizing Ab titers to clinical outcome, there is a need for new to diagnostic methods, devices and kits for detecting neutralizing antibodies to SARS-CoV-2.

SUMMARY

Provided herein are methods for detection and measurement of neutralizing antibody levels to a coronavirus (e.g., SARS-CoV-2, and the like) in a test-specimen, said method comprising:
  obtaining a test-specimen from a subject;
  transferring the test-specimen to a sample well of a test-cassette, wherein the cassette further comprises a sample pad, a conjugate pad, a nitrocellulose membrane and an absorbent pad, wherein the sample pad comprises ACE2 or a functional fragment thereof, wherein the conjugate pad comprises a viral-ACE2-binding protein coupled to a label;
  adding a buffer; and
  reading the results from the test-cassette.

The invention methods are useful herein: to test pre-collected convalescent plasma form patients known to have had COVID19; to test a pre-donated sample using a drop of blood (e.g., 10 microliter drop) from a lancet finger-stick from a patient known or suspected of having been infected with COVID19; and/or as a post-vaccine companion diagnostic to determine whether and how much vaccine administration has produced neutralizing antibodies to SARS-CoV-2.

In one embodiment, the invention diagnostic method is referred to herein as the IMMUNOPASS diagnostic method. The IMMUNOPASS SARS-Cov-2 Neutralizing Antibody Rapid Test is a rapid test that utilizes a combination of SARS-COV-2 antigen coated colored particles and a modified human ACE2 protein receptor for the detection of antibodies to SARS-COV-2 in serum or plasma that block interaction of the virus with human cells expressing ACE2. IMMUNOPASS is a rapid point of care test that measures relative levels of antibodies (e.g., neutralizing antibodies referred to herein as NAbs) against Spike protein receptor binding domain (RBD) that block it from binding to ACE2 cellular receptor. Such antibodies have been shown in peer-reviewed publications to neutralize virus and will be referred to as "neutralizing antibodies". Neutralizing antibodies may be any isotype. In certain embodiments, the invention IMMUNOPASS lateral flow test can be used for rapid detection of neutralizing antibodies to SARS-CoV-2 in plasma, serum or whole blood. "Recovered" indicates individuals have become PCR negative and may have tested positive in a COVID19 serology test for total Ig or IgG.

The invention IMMUNOPASS diagnostic test is intended for semi-quantitative measurement of neutralizing antibody levels in plasma or serum from individuals who have had recent or prior infection with SARS-CoV-2 and who have recovered from COVID19 and individuals who have received a COVID19 vaccine. The invention methods and products are useful as clinical decision-making tools for therapeutic administration of convalescent plasma for treatment of patients fighting COVID19.

Because several publications have shown that >30% of COVID19 convalescent plasma does not neutralize SARS-CoV-2 in either spike protein pseudotype or authentic SARS-CoV-2 plaque reduction neutralization assays, the IMMUNOPASS test advantageously addresses the question of whether convalescent plasma from recovered COVID19 patients contains neutralizing antibodies suitable for administration to patients actively fighting COVID19. In typical embodiments, the test should be performed with positive and negative controls. Currently, it is unknown for how long antibodies persist following infection, but the invention IMMUNOPASS methods, devices and kits provide the ability to accurately measure levels of neutralizing antibodies in convalescent plasma.

The results described herein are for the semi-quantitative measurement of antibodies which neutralize SARS-CoV-2. Antibodies to SARS-CoV-2 are generally detectable in blood several days after initial infection, although the duration of time antibodies are present post-infection is not well characterized. Individuals may have detectable virus present for several weeks following seroconversion. Detection and measurement of high levels of neutralizing antibodies may limit virus transmission and protect individuals from re-infection.

In particular embodiments, the test-specimen is whole blood, plasma or serum. In certain embodiments, the whole blood, plasma or serum is obtained from a patient either known or suspected of recovering from COVID19 disease;

or known to have been vaccinated for SARS-CoV-2. In particular embodiments, the plasma is obtained using anticoagulants such as heparin, dipotassium EDTA or sodium citrate, and the like.

In certain embodiments, wherein the test-specimen is whole blood, plasma, serum and/or saliva. In particular embodiments, the whole blood, plasma, serum or saliva is obtained from a patient either known or suspected of recovering from COVID19 disease; or known to have been vaccinated for SARS-CoV-2. In certain embodiments, ACE2 is bound directly on the sample pad, or in other embodiments, ACE2 is bound to the sample pad via a tag/anti-tag pair. In a particular embodiment, ACE2 is bound to biotin; and the sample pad is bound to streptavidin. In typical embodiments, the viral-ACE2-binding protein is an RBD.

In certain embodiments, the plasma is obtained using an anticoagulant. In yet further embodiments, the anticoagulant is selected from the group consisting of: heparin, dipotassium EDTA or sodium citrate. In particular embodiments, the label is selected from a nanoparticle, bead, latex bead, aptamer, and/or a quantum dot. In another embodiment, the conjugate pad further comprises a mixture of RBD coupled to a nanoparticle and control-antibody coupled to a nanoparticle. In one embodiment, the RBD is coupled to a gold nanoshell (GNS) and the control-antibody is a monoclonal antibody (e.g., a mouse Mab, or the like) coupled to a gold nanosphere (GNP). In particular embodiments, reading the results from the test-cassette further comprises determining the intensity of a test-line in the test-cassette compared with a reference standard. In a particular embodiment, the reference standard is a scorecard.

In certain embodiments, the level of anti-SARS-CoV-2 NAbs in the test-specimen is reported as falling within a range of pre-determined values. In a particular embodiment, the range of pre-determined values corresponds to high, moderate or low/non-neutralizing relative to three respective controls. In another embodiment, the range of pre-determined values corresponds to High (H), Moderate-High (MH), Moderate to Moderate-High (M-MH), Moderate (M), Moderate to Not Detectable (M-ND) and Not Detectable (ND).

Also provided herein are methods of determining the levels of protective neutralizing antibodies induced by a SARS-CoV-2 vaccination or infection of a particular subject, comprising:
obtaining a test-specimen from a subject, wherein the subject was previously vaccinated; or known or suspected to have been previously infected with SARS-CoV-2; and
detecting the presence and/or quantity of NAb according to methods provided herein for detection of neutralizing antibodies to SARS-CoV-2 in a test-specimen.

In certain embodiments, the subject was vaccinated or infected prior to obtaining the test-specimen in the range of: 1-365 days, 2-300 days, 3-275 days, 4-250 days, 5-225 days, 6-200 days, 7-180 days, 8-180 days, 9-180 days, 10-180 days, 11-180 days, 12-180 days, 13-180 days, and/or 14-180 days. In typical embodiments, detecting the presence of NAbs above a threshold value indicates protective antibody-based vaccination or infection.

Also provided herein are methods of identifying high-titer anti-SARS-CoV-2 NAbs samples induced by SARS-CoV-2 vaccination or infection of a particular subject, comprising:
obtaining a test-specimen from a subject, wherein the subject was previously vaccinated; or known or suspected to have been previously infected with SARS-CoV-2; and
detecting the presence and/or quantity of NAb according to methods provided herein for detection of neutralizing antibodies to SARS-CoV-2 in a test-specimen.

Also provided herein are methods of measuring neutralizing antibody levels to SARS-CoV-2 in a specimen using an electronic device, said method comprising:
scanning a code into the electronic device that identifies a test to be performed and a particular specimen to be tested;
conduct the method of detecting the presence and/or quantity of NAb according to methods provided herein for detection of neutralizing antibodies to SARS-CoV-2 in a test-specimen; and
scanning the results obtained from the test-cassette into the electronic device.

In typical embodiments, the results are processed directly on the electronic device. In particular embodiments the electronic device is a smartphone, tablet or personal computer. In other embodiments, the electronic device further connects to a database, thereby transferring the results to said database. In certain embodiments, the device connects to the database via email, WiFi, SMS, worldwide web, 4G, 5G, Bluetooth and/or USB.

Also provided herein are SARS-CoV-2 test-cassette devices, comprising a sample pad, a conjugate pad, a nitrocellulose membrane and an absorbent pad, wherein the sample pad and/or conjugate pad comprises ACE2 or a functional fragment thereof, and wherein the conjugate pad comprises a viral-ACE2-binding protein coupled to a label. In certain embodiments, the ACE2 is bound directly on the sample pad and/or conjugate pad; or ACE2 is bound to the sample pad and/or conjugate pad via a tag/anti-tag pair. In particular embodiments, ACE2 is bound to biotin; and the nitrocellulose membrane is bound to streptavidin. In particular embodiments, the viral-ACE2-binding protein is an RBD. In yet other embodiments, the conjugate pad further comprises a mixture of RBD coupled to a nanoparticle and control-antibody coupled to a nanoparticle. In other embodiments, the RBD is coupled to a gold nanoshell (GNS) and the control-antibody is a monoclonal antibody coupled to a gold nanosphere (GNP).

In particular embodiments, a whole-blood filter is present in lieu of the sample pad. In certain embodiments, the conjugate pad comprises a viral-ACE2-binding protein coupled to a label; and further comprises ACE2 or a functional fragment thereof. In particular embodiments, the ACE2 or functional fragment thereof is spatially separated from the viral-ACE2-binding protein. In one embodiment, the viral-ACE2-binding protein is an RBD region of a SARS-CoV-2 spike protein.

Also provided herein are SARS-CoV-2 test-cassette devices, comprising a whole blood filter, a conjugate pad, a nitrocellulose membrane and an absorbent pad, wherein the conjugate pad comprises ACE2 or a functional fragment thereof, and a viral-ACE2-binding protein coupled to a label. In certain embodiments, ACE2 is bound directly on the conjugate pad; or ACE2 is bound to the conjugate pad via a tag/anti-tag pair. In other embodiments, ACE2 is bound to biotin; and the nitrocellulose membrane is bound to streptavidin. In a particular embodiment, the viral-ACE2-binding protein is an RBD. In certain embodiments, the conjugate pad further comprises a mixture of RBD coupled to a nanoparticle and control-antibody coupled to a nanoparticle. In yet further embodiments, the RBD is coupled to a gold nanoshell (GNS) and the control-antibody is a monoclonal antibody coupled to a gold nanosphere (GNP). In yet other embodiments, the ACE2 or functional fragment thereof is spatially separated from the viral-ACE2-binding protein. In one embodiment, the viral-ACE2-binding protein is an RBD region of a SARS-CoV-2 spike protein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8A shows an interpretation of results of a test strip after undergoing an invention diagnostic assay.

FIG. 8B also shows an interpretation of results of a test strip after undergoing an invention diagnostic assay.

FIG. 13A shows a plasma panel regarding the differences between Whole Blood vs Plasma Assay Embodiments of the invention test-cassette devices.

FIG. 13B. shows a whole blood panel regarding the differences between Whole Blood vs Plasma Assay Embodiments of the invention test-cassette devices.

DETAILED DESCRIPTION

Figure 1:
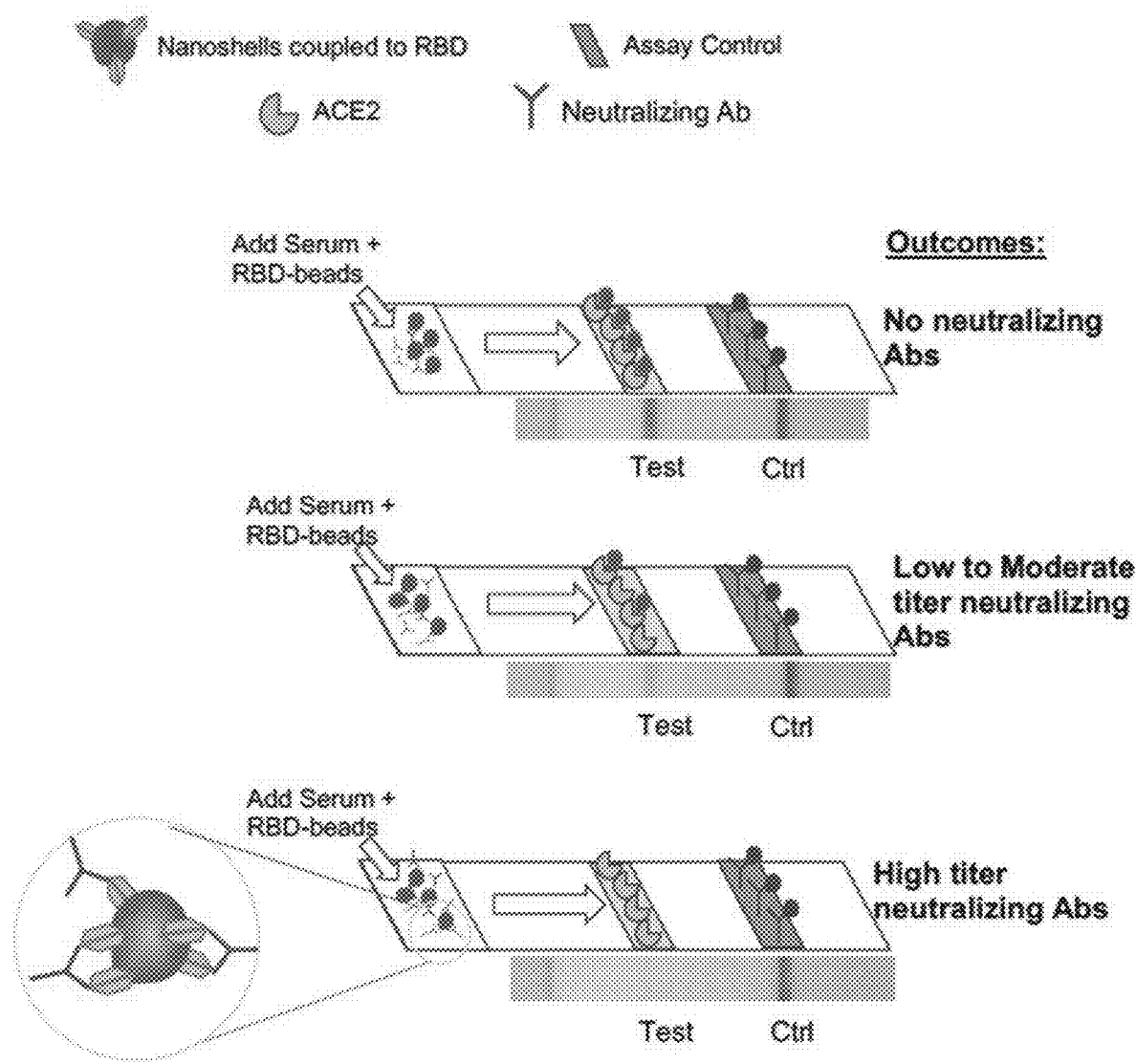
FIG. 1 shows a schematic of one embodiment of the invention IMMUNOPASS Neutralization LFA. Below each graphic is a representative image of a lateral flow strip demonstrating actual line density. Addition of non-COVID19-immune serum or plasma (top) does not block binding of RBD-beads to ACE2 resulting in the RBD-bead-ACE2 complex creating a visible line. Addition of moderate titer NAbs to the sample pad creates a weak line (middle). Addition of high titer NAbs (>1:640) blocks binding of RBD-beads to ACE2 such that no line is observed at the test location on the strip (bottom). Red control line represents capture of gold nanospheres coupled to a monoclonal antibody (e.g., a mouse Mab, or the like).
Figure 2A:
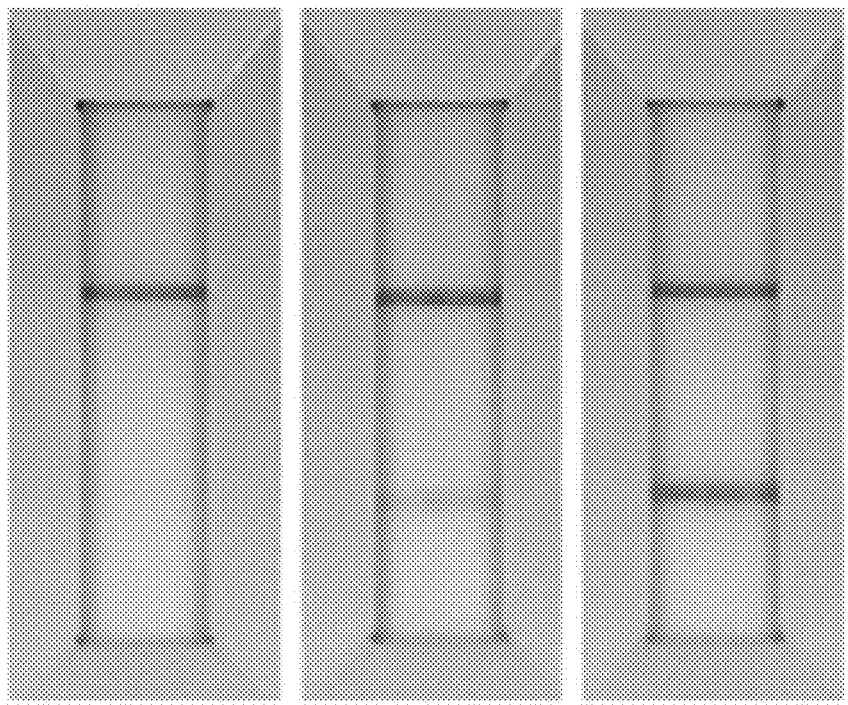
FIG. 2A shows one embodiment of an IMMUNOPASS Scorecard for measuring 3 relative levels of neutralizing antibodies in plasma or serum.
Figure 2B:
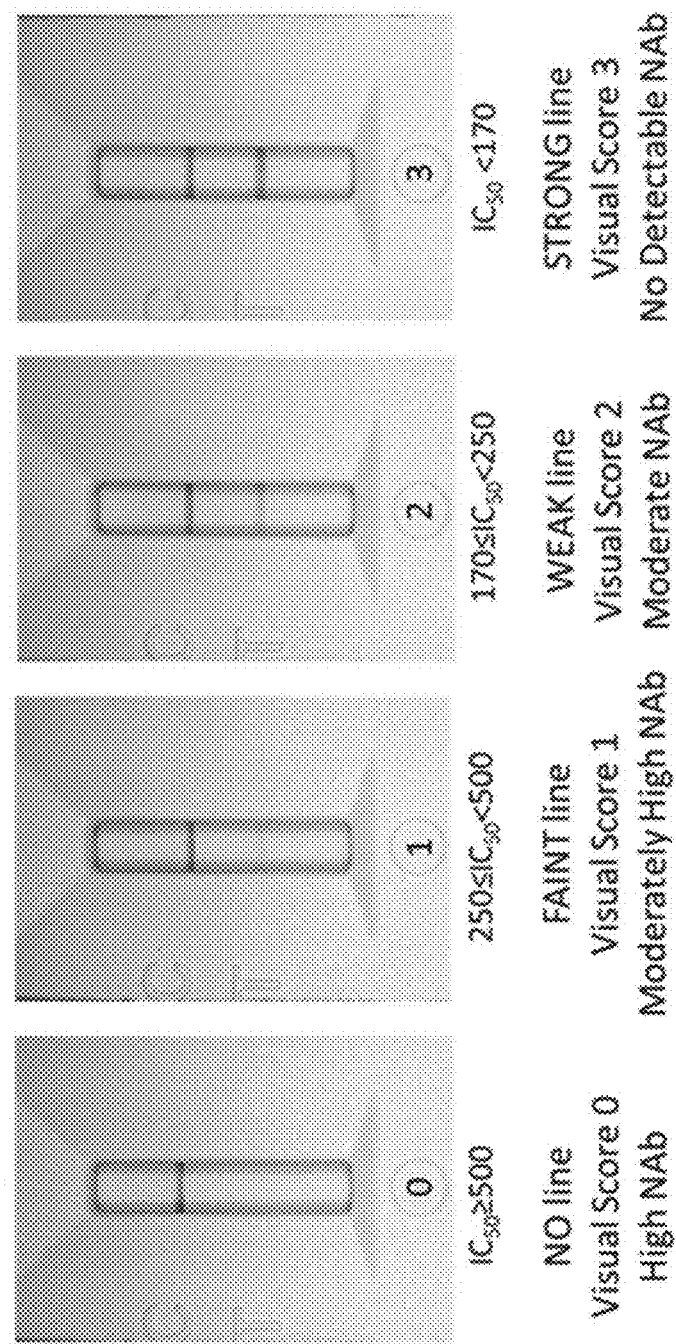
FIG. 2B shows one embodiment of an IMMUNOPASS Scorecard for measuring 4 relative levels of neutralizing antibodies in plasma or serum FIG. 3A corresponds to the internal placement of general exemplary components of a particular embodiment of an IMMUNOPASS lateral flow strip cassette.

Provided herein are methods for detection and measurement of neutralizing antibody levels to a coronavirus (e.g., SARS-CoV-2, and the like) in a test-specimen, said method comprising:

obtaining a test-specimen from a subject;

transferring the test-specimen to a sample well of a test-cassette, wherein the cassette further comprises a sample pad, a conjugate pad, a nitrocellulose membrane and an absorbent pad, wherein the sample pad comprises ACE2 or a functional fragment thereof, wherein the conjugate pad comprises a viral-ACE2-binding protein coupled to a label;

adding a buffer; and reading the results from the test-cassette.

In certain embodiments, the present invention provides and utilizes compositions and materials for conducting a lateral flow assay (e.g., a lateral flow immunoassay). Lateral flow assays are based on the principles of immunochromatography and can be used to detect, quantify, test, measure, and monitor a wide array of analytes, pathogens (e.g., SARS-CoV-2), and the like.

Neutralizing antibodies identified using the disclosed methods can specifically bind to any known or as yet undiscovered coronavirus, such as, for example, coronavirus OC43, coronavirus 229E, coronavirus NL63, coronavirus HKU1, MERS-CoV, SARS-CoV, or SARS-CoV-2 (COVID-19). In some embodiments, the neutralizing antibodies are directed against SARS-CoV-2 (COVID-19). In the context of the present disclosure a "neutralizing antibody" is an antibody that binds to a virus (e.g., a coronavirus) and interferes with the virus' ability to infect a host cell. Coronavirus spike proteins are known to elicit potent neutralizing-antibody and T-cell responses. The ability of a virus (e.g., coronavirus OC43, coronavirus 229E, coronavirus NL63, coronavirus HKU1, MERS-CoV, SARS-CoV, or SARS-CoV-2 (COVID-19)) to gain entry into cells and establish infection is mediated by the interactions of its "viral-ACE2 binding protein" (e.g., Spike glycoproteins, and the like) with human cell surface receptors.

As used herein, the phrase "viral-ACE2 binding protein" refers to any full length protein, functional fragment thereof (e.g., an RBD domain, and the like) that functions to bind to ACE2 (e.g., human ACE2) to facilitate gaining entry into cells to establish a coronavirus infection, e.g., a SARS-Cov-2 infection. Exemplary viral-ACE2 binding proteins are well-known in the art, and include spike proteins (e.g., SARS CoV-2 spike protein) or RBD domains thereof, and the like. In the case of coronaviruses, Spike proteins are large type I transmembrane protein trimers that protrude from the surface of coronavirus virions. Each Spike protein comprises a large ectodomain (comprising S1 and S2), a transmembrane anchor, and a short intracellular tail. The S1 subunit of the ectodomain mediates binding of the virion to host cell-surface receptors through its receptor-binding domain (RBD). The S2 subunit fuses with both host and viral membranes, by undergoing structural changes.

SARS-CoV-2 utilizes the Spike glycoprotein to interact with cellular receptor ACE2 (Zhou et al., Nature 579: 270-273, doi:10.1038/s41586-020-2012-7 (2020); Hoffmann et al., Cell, 50092-8674(0020)30229-30224, doi: 10.1016/j.cell.2020.02.052 (2020) doi:10.1016/j.cell.2020.02.052 (2020). The amino acid sequence of the SARS-CoV-2 spike protein has been deposited with the National Center for Biotechnology Information (NCBI) under Accession No. QHD43416. Binding with ACE2 triggers a cascade of cell membrane fusion events for viral entry. The high-resolution structure of SARSCoV-2 RBD bound to the N-terminal peptidase domain of ACE2 has recently been determined, and the overall ACE2-binding mechanism is virtually the same between SARS-CoV-2 and SARS-CoV RBDs, indicating convergent ACE2-binding evolution between these two viruses (Gui et al., CellRes 27, 119-129, doi:10.1038/cr.2016.152 (2017); Song et al., PLoS Pathog 14, e1007236-e1007236, doi:10.1371/journal.ppat.1007236 (2018); Yuan et al., Nat Commun 8, 15092-15092, doi: 10.1038/ncomms15092 (2017); and Wan et al., J Virol, JVI.00127-00120, doi:10.1128/JVI.00127-20 (2020)). This suggests that disruption of the RBD and ACE2 interaction, e.g., by neutralizing antibodies, would block SARS-CoV-2 entry into the target cell. Indeed, a few such disruptive agents targeted to ACE2 have been shown to inhibit SARS-CoV infection (Kruse, R. L., F1000Res, 9: 72-72; doi: 10.12688/f1000research.22211.2 (2020); and Li et al., Nature 426, 450-454; doi:10.1038/nature02145 (2003)). In addition, neutralizing antibodies directed against coronaviruses (also referred to herein as "coronavirus neutralizing antibodies") have been identified and isolated (see, e.g., Liu et al., Potent neutralizing antibodies directed to multiple epitopes on SARS-CoV-2 spike. Nature (2020). doi.org/10.1038/s41586-020-2571-7; Rogers et al., Science 15 Jun. 2020:eabc7520; DOI: 10.1126/science.abc7520; Alsoussi et al., J Immunol Jun. 26, 2020, ji2000583; DOI:/doi.org/10.4049/jimmunol.2000583; Kreer et al., Cell, S0092-8674 (20)30821-7. 13 Jul. 2020, doi:10.1016/j.cell.2020.06.044; Tai et al., J Virol. 2017 Jan. 1; 91(1): e01651-16; and Niu et al., J Infect Dis. 2018 Oct. 15; 218(8): 1249-1260).

The peptide comprising a receptor binding domain (RBD) of a coronavirus spike protein may be prepared using routine molecular biology techniques, such as those disclosed herein. The nucleic acid and amino acid sequences of RBDs of various coronavirus spike proteins are known in the art (see, e.g., Tai et al., Cell Mol Immunol 17, 613-620 (2020). doi.org/10.1038/s41423-020-0400-4; and Chakraborti et al., Virology Journal volume 2, Article number: 73 (2005); and Chen et al., Biochemical and Biophysical Research Communications, 525(1): 135-140 (2020)). An exemplary RBD domain of a SARS-CoV-2 spike protein comprises the following amino acid sequence:

(SEQ ID NO: 1)
RVQPTESIVRFPNITNLCPFGEVFNATRFASVYAWNRKRISNCVADYSVL

YNSASFSTFKCYGVSPTKLNDLCFTNVYADSFVIRGDEVRQIAPGQTGKI

ADYNYKLPDDFTGCVIAWNSNNLDSKVGGNYNYLYRLFRKSNLKPFERDI

STEIYQAGSTPCNGVEGFNCYFPLQSYGFPTNGVGYQPYRVVVLSFELLH

APATVCGPKKSTNLVKNKCVNFNFNGLTGTGVLTESNKKFLPFQQFGRDI

ADTTDAVRDPQTLEILDITPCS.

In other particular embodiments, an exemplary sequence used herein for the RBD domain corresponds to amino acids 319-541 of SARS-CoV-2 Spike, set forth as follows:
QRVQPTESIVRFPNITNLCPFGEVFNATR-
FASVYAWNRKRISNCVADYSVLYNSASFS
TFKCYGVSPTKLNDLCFTNVYADSFVIR-
GDEVRQIAPGQTGKIADYNYKLPDDFTGC
VIAWNSNNLDSKVGGNYNYLYRLFRKSNLKPFERD-
ISTEIYQAGSTPCNGVEGFNCY
FPLQSYGFQPTNGVGYQPYRVVVLSFELL-
HAPATVCGPKKSTNLVKNKCVNF (SEQ ID NO:2). Those skill in the art will recognize that functional fragments of SEQ ID NO:1 and/or SEQ ID NO:2 can also be used in the invention methods and devices.

In particular embodiments, the test-specimen is whole blood, plasma or serum. In another embodiment, the test-specimen can also be obtained from saliva. In certain embodiments, the whole blood, plasma or serum is obtained from a patient either known or suspected of recovering from COVID19 disease; or known to have been vaccinated for SARS-CoV-2. In particular embodiments, the plasma is obtained using anti-coagulants such as heparin, dipotassium EDTA or sodium citrate, and the like.

In certain embodiments, wherein the test-specimen is whole blood, plasma, serum and/or saliva. In particular embodiments, the whole blood, plasma, serum or saliva is obtained from a patient either known or suspected of recovering from COVID19 disease; or known to have been vaccinated for SARS-CoV-2. In certain embodiments, ACE2 is bound directly on the sample pad, or in other embodiments, ACE2 is bound to the sample pad via a tag/anti-tag pair.

In particular embodiments, an exemplary sequence used herein for the ACE2 domain corresponds to amino acids 18-615 of the full-length human ACE2, set forth as follows:

(SEQ ID NO: 3)
QSTIEEQAKTFLDKENHEAEDLEYQSSLASWNYNTNITEENVQNMNNAGD

KWSAFLKEQSTLAQMYPLQEIQNLTVKLQLQALQQNGSSVLSEDKSKRLN

TILNTMSTIYSTGKVCNPDNPQECLLLEPGLNEIMANSLDYNERLWAWES

WRSEVGKQLRPLYEEYVVLKNEMARANHYEDYGDYWRGDYEVNGVDGYDY

SRGQLIEDVEHTFEEIKPLYEHLHAYVRAKLMNAYPSYISPIGCLPAHLL

GDMWGRFWTNLYSLTVPFGQKPNIDVTDAMVDQAWDAQRIFKEAEKFFVS

VGLPNMTQGFWENSMLTDPGNVQKAVCHPTAWDLGKGDFRILMCTKVTMD

DFLTAHHEMGHIQYDMAYAAQPFLLRNGANEGFHEAVGEIMSLSAATPKH

LKSIGLLSPDFQEDNETEINFLLKQALTIVGTLPFTYMLEKWRWMVFKGE

IPKDQWMKKWWEMKREIVGVVEPVPHDETYCDPASLFHVSNDYSFIRYYT

RTLYQFQFQEALCQAAKHEGPLHKCDISNSTEAGQKLFNMLRLGKSEPWT

LALENVVGAKNMNVRPLLNYFEPLFTWLKDQNKNSFVGWSTDWSPYAD

Those skill in the art will recognize that functional fragments of SEQ ID NO:3 can also be used in the invention methods and devices.

As used herein the term "tag/anti-tag pair" or vice versa (anti-tag/tag pair) refers to 2 moieties that are known to bind (e.g., non-covalently) to each other. For example, tag/anti-tag pairs can be ligand/receptor pairs; where the anti-tag is the binding partner to the tag. In an embodiment, the ACE2 or functional fragment thereof (referred to herein as ACE2 for simplicity) binds to the nitrocellulose membrane through a tag/anti-tag interaction during the assay. In another embodiment, the ACE2 is bound to the nitrocellulose membrane through a tag/anti-tag interaction prior to the assay, for example during manufacturing of or preparation of the assay. The tag/anti-tag interaction can be a noncovalent interaction, such as a protein-ligand interaction. In an embodiment, the noncovalent protein-ligand interaction is an interaction between biotin and avidin or streptavidin.

Biotin is conjugated to ACE2, and avidin or streptavidin is conjugated to the nitrocellulose membrane. The high-affinity interaction between biotin and avidin or streptavidin tethers the biotin-ACE2 conjugate to the streptavidin-conjugated sample pad such that the ACE2 is then available to be bound by the viral ACE2-binding protein from the conjugate pad. Streptavidin is a tetramer and each subunit binds biotin with equal affinity; thus, wild-type streptavidin binds four biotin molecules. For some applications it is useful to generate a strong 1:1 complex of two molecules, i.e., monovalent binding. Monovalent streptavidin is an engineered recombinant form of streptavidin which is still a tetramer but only one of the four binding sites is functional. A streptavidin with exactly two biotin binding sites per tetramer (divalent streptavidin) can be produced by mixing subunits with and without a functional biotin binding site. A streptavidin with exactly three biotin binding sites per tetramer (trivalent streptavidin) can also be produced using the same principle as to produce divalent streptavidins. The streptavidin used in the inventive assay can be wild-type (binding four biotins), or it may be monovalent, divalent, or trivalent. Methods of conjugating biotin and streptavidin to proteins and substrates are known to those of skill in the art and any such methods can be used to conjugate biotin or streptavidin to ACE2, and to conjugate biotin or streptavidin to the sample pad.

In another embodiment, the noncovalent protein-ligand interaction is a Halo interaction. Halo-Tag is a 33 kDa mutagenized haloalkane dehalogenase that forms covalent attachments to substituted chloroalkane linker derivatives (Halo-Ligand). Similarly to the streptavidin-biotin connection, the chloroalkane linker extends 1.4 nm into the hydrophobic core of Halo-Tag. Commercially available Halo-ligand derivatives include the invariant chloroalkane moiety followed by 4 ethylene glycol repeats, and a reactive sulfahydryl, succinimidyl ester, amine, or iodoacetamide group, among many other options. Methods of conjugating biotin and streptavidin to proteins and substrates are known to those of skill in the art and any such methods can be used to conjugate Halo-Tag or Halo-Ligand to ACE2, and to Halo-Tag or Halo-Ligand to the sample pad.

In another embodiment, the noncovalent protein-ligand interaction is a His-tag interaction. The His-tag (also called 6×His-tag) contain six or more consecutive histidine residues. These residues readily coordinate with transition metal ions such as Ni2+ or Co2+ immobilized on beads or a resin. The His-tag is added to the recombinant ACE2 used in the assay, with the beads or resin with immobilized Ni2+ or Co2+ conjugated or otherwise bound to the nitrocellulose membrane. Methods of adding His-tags to proteins and beads or resin with immobilized Ni2+ or Co2+ to substrates are known to those of skill in the art and any such methods can be used to add a His-tag to ACE2, and beads or resin with immobilized Ni2+ or Co2+ to the nitrocellulose membrane. In other embodiments, the noncovalent interaction utilizes a ligand tag that is calmodulin-binding peptide, glutathione, amylose, a c-my tag, or a Flag tag. The ligand tag is attached to the ACE2, and the respective ligand-binding molecule is attached to the nitrocellulose membrane using methods known to those of skill in the art. The ligand tag can also be single-strand DNA (ssDNA) attached to the ACE2, where the complementary ssDNA is immobilized on the nitrocellulose membrane.

In another embodiment, the ACE2 is directly bound to the nitrocellulose membrane via covalent bonding. In an embodiment, the covalent bond is amine-glutaraldehyde-amine, where an amine group on ACE2 is conjugated to an amine group either natively present or introduced on the surface of the membrane. In an embodiment, the covalent bond is amine-NHS (N-hydroxysuccinimide), where NHS ester is used as a covalent linking agent. In an embodiment, the covalent bond is carboxylate-1-ethyl-3-(3-dimethylaminopropyl) carbodiimide (EDC)-amine, where carbodiimide is used to form amide linkage between carboxylates and amines. In other embodiments, the covalent bond is carboxylate-EDC+NETS-amine. In an embodiment, the covalent bond is amine/sulfhydryl-epoxide, where epoxides form covalent bonds with primary amines at mild alkaline pH or with sulfhydryl groups (—SH) in the physiological pH range. In an embodiment, the covalent bond is amine-isothiocyanate, where the reaction of an aromatic amine with thiophosgene (CSCl2) yields isothiocyanate (—NCS), which forms a stable bond with primary amine groups. In another embodiment, the covalent bond is amine-azlactone, where azlactone is used to react with nucleophiles such as amines and thiols at room temperature to form amide bonds. In an embodiment, the covalent bond is amine-p-nitrophenyl ester, where p-nitrophenyl ester is reactive to amines across the slightly basic pH range spanning 7-9 and the ester forms a stable amide bond with proteins. In an embodiment, the covalent bond is amine-tyrosinase (TR)-tyrosine. Tyrosinase is a phenol oxidase that oxidizes phenols into 0-quinone (i.e., 1,2-benzoquinone), which is reactive and undergoes reaction with various nucleophiles such as primary amines. In another embodiment, the covalent bond can be sulfhydryl-maleimide, where maleimide is used to form covalent links with the cysteine residues of proteins. In another embodiment, the covalent bond is reactive hydrogen-benzophenone, where during UV exposure, the benzophenone couples with a protein via reactive hydrogen compounds on the protein. When the benzophenone residues are incorporated onto sample pad, the ACE2 can be immobilized to the surface of the sample pad via exposure to UV light. The particular methods of applying these covalent bonding chemistries to conjugation of proteins is known to those of skill in the art. Multiple covalent bonding chemistries can be used together, including with bifunctional linkers, as known to those of skill in the art. An enormous variety of covalent conjugation chemistries beyond those listed here are known to those of skill in the art. See, for example Kim et al. Biomicrofluidics 7, 041501 (2013), Rusmini et al. Biomacromolecules 8, 1775 (2007), and Hermansson Bioconjugate Techniques, 2nd ed. (Academic Press, San Diego, 2008), all incorporated herein by reference.

The covalent bonding chemistries described above are useful not only for directly conjugating ACE2 to the nitrocellulose membrane, but also for conjugating the respective molecules for noncovalent interactions to ACE2 or to the nitrocellulose membrane, for example for conjugating biotin to ACE2 and/or for conjugating avidin or streptavidin to the nitrocellulose membrane. Additionally, spacers such as polyethylene glycol (PEG) chains can be used together with the linkers for such covalent conjugation (e.g., PEG-NETS) to provide space between the ACE2 and nitrocellulose membrane, and/or ACE2 and biotin, and/or avidin or streptavidin and nitrocellulose membrane. Such spacing can be used to provide the ACE2 with more freedom of movement relative to the nitrocellulose membrane and thus greater opportunity to interact with the viral ACE2-binding protein and/or neutralizing antibodies.

In a particular embodiment, ACE2 is bound to biotin; and the sample pad is bound to streptavidin. In typical embodiments, the viral-ACE2-binding protein is an RBD.

In certain embodiments, the plasma is obtained using an anticoagulant. In yet further embodiments, the anticoagulant is selected from the group consisting of: heparin, dipotassium EDTA or sodium citrate.

As used herein, the term "label" refers to a moiety, the presence of which can be detected using methods well-known in the art for label-detection. In an embodiment, the viral ACE2-binding protein is coupled to a label such that it can be detected when bound to the ACE2 bound to the nitrocellulose membrane, thus demonstrating a lack of neutralizing antibodies in the sample. In an embodiment, the control protein (for example, an anti-IgG monoclonal antibody) is coupled to a label such that it can be detected when bound to its target on the nitrocellulose membrane (for example, IgG), thus demonstrating that the test is functional and has been performed properly. In an embodiment, the viral ACE2-binding protein and control protein are coupled to different labels. In an embodiment, the label for the viral ACE2-binding protein and/or that for the control protein is detectable by the naked eye. In another embodiment, the label for the viral ACE2-binding protein and/or that for the control protein is detectable by fluorescence. In another embodiment, the label for the viral ACE2-binding protein and/or that for the control protein is detectable by chemiluminescence. Methods for coupling the labels to proteins are known to those of skill in the art.

Labels detectable by the naked eye include metal nanoparticles and nanoshells (e.g., green gold nanoshells; red, orange, or blue gold nanoparticles; copper oxide nanoparticles; silver nanoparticles), gold colloid, platinum colloid, polystyrene latex or natural rubber latex colored with respective pigments such as red and blue. Labels detectable by the naked eye include textile dyes, such as for example, a Direct dye, a Disperse dye, a Dischargeable acid dye, a Kenanthol dye, a Kenamide dye, a Dyacid dye, a Kemtex reactive dye, a Kemtex acid dye, a Kemtex Easidye acid dye, a Remazol dye, a Kemazol dye, a Caledon dye, a Cassulfon dye, an Isolan dye, a Sirius dye, an Imperon dye, a phtalogen dye, a naphtol dye, a Levafix dye, a Procion dye, and an isothiocyanate dye. Examples of textile dyes that can be used to label proteins include, for example, Remazol brilliant blue, Uniblue A, malachite green isothiocyanate, and Orange 16 (Remazol orange). Any label known to those of skill in the art to both be fluorescent and used to label proteins can be used.

Fluorescent labels include any of the Alexa fluor dyes, any of the BODIPY dyes, any of the eFluor dyes, any of the Super Bright dyes, fluorescein or a derivative thereof, eosin or a derivative thereof, tetramethylrhodamine, rhodamine or a derivative thereof, Texas red or a derivative thereof, pyridyloxazole or a derivative thereof, NBD chloride, NBD fluoride, ABD-F, lucifer yellow or a derivative thereof, 8-anilino-1-naphthalenesulfonic acid (8-ANS) or a derivative thereof, Oregon green or a derivative thereof, Pacific blue or a derivative thereof, Pacific green or a derivative thereof, Pacific orange or a derivative thereof Cy3, Cy5, Cyanine7, Cyanine5.5, or coumarin or a derivative thereof. Fluorescent labels include any fluorescent protein, such as green fluorescent protein (GFP), red fluorescent protein (e.g., dsRed), cyan fluorescent protein, blue fluorescent protein, yellow fluorescent protein, enhanced green fluorescent protein (EGFP), or any derivative of such fluorescent proteins thereof. Any label known to those of skill to both be fluorescent and be used to label proteins can be used.

Chemiluminescent labels include enzyme labels that catalyze formation of ATP which is then assayed by the firefly reaction or that catalyze formation of peroxide which is determined by luminol, isoluminol, or peroxyoxalate CL. Such enzyme labels include luciferase and horseradish peroxidase. Any label known to those of skill in the art to both be chemiluminescent and used to label proteins can be used.

In particular embodiments, the label is selected from a nanoparticle, bead, latex bead, aptamer, oligonucleotides, proteins and/or a quantum dot. In another embodiment, the conjugate pad further comprises a mixture of RBD coupled to a nanoparticle and control-antibody coupled to a nanoparticle. In one embodiment, the RBD is coupled to a gold nanoshell (GNS) and the control-antibody is a monoclonal antibody (e.g., a mouse Mab, or the like) coupled to a gold nanosphere (GNP). In particular embodiments, reading the results from the test-cassette further comprises determining the intensity of a test-line in the test-cassette compared with a reference standard.

As used herein, the phrase "reference standard" refers to a control set of values, either obtained simultaneously with the assay results or obtained from a previous control experiment such they they are indicative of the level of NAbs present in the test-specimen (see, e.g., FIG. 2A, FIG. 2B, FIG. 8A, FIG. 8B, FIG. 9A, FIG. 9B, FIG. 11, FIG. 12, or the like). In a particular embodiment, the reference standard is a scorecard.

In certain embodiments, the level of anti-SARS-CoV-2 NAbs in the test-specimen is reported as falling within a range of pre-determined values. As used herein, the phrase "reported as falling within a range of pre-determined values" refers to the manner in which the level of anti-RBD NAbs are analyzed relative to the reference standard or set of control values. The range of pre-determined values can be as few as two levels of NAb values (or concentrations) up top about 10 or more distinct concentration (or quantity) levels of NAbs present in the test-specimen. In one embodiment corresponding to 2 levels of Nab values, for example, falling either above or below a predetermined set value may indicate the presence of sufficient protective anti-RBD NAbs, such that there is a greater likelihood there is protection from getting a subsequent coronavirus infection. In another embodiment, a particular embodiment, the range of pre-determined values corresponds to high, moderate or low/non-neutralizing relative to three respective controls (see FIG. 2A). In another embodiment, the range of pre-determined values corresponds to High (H), Moderate-High (MH), Moderate to Moderate-High (M-MH), Moderate (M), Moderate to Not Detectable (M-ND) and Not Detectable (ND) (see FIG. 2B). Thus, those of skill in the art will appreciated that any number of NAb concentrations and/or quantity levels can be used to identify particular test-specimens being assayed for particular purposes, e.g., those test-specimens above a specified level can be advantageously useful in convalescent therapy In a particular embodiment, the invention methods are referred to herein as the IMMUNOPASS SARS-Cov-2 Neutralizing Antibody Rapid Test is a lateral flow immunochromatographic assay for semi-quantitative measurement of antibodies that neutralize SARS-CoV-2 in human serum or plasma (see FIG. 1). In a particular embodiment, this test uses immobilized polystreptavidin (test line T) and goat anti-mouse IgG (control line C) on a nitrocellulose strip. In other embodiments, the conjugate pad contains recombinant SARS-CoV-2 antigen (Spike protein RBD domain from SARS-CoV-2) conjugated with dark green gold Nanoshells and a mouse antibody conjugated to red gold Nanospheres. The sample pad contains tagged (e.g., biotinylated) human ACE2 protein.

During testing, in a particular embodiment, anti-RBD antibodies in plasma or serum bind to RBD-conjugated dark green gold Nanoshells in the test cassette. When assay (chase) buffer is added to the sample well, the dried components on the strip interact with plasma or serum from whole blood. If the sample contains antibodies that prevent RBD from binding to ACE2 (neutralizing antibodies), the test will show a light or ghost Test line. If the sample does not contain, or contains low levels of neutralizing antibodies, RBD-gold Nanoshells and ACE2-biotin will interact forming a dark green Test line.

To serve as a procedural control, a colored line should always appear in the control line region, indicating that the proper volume of specimen has been added and membrane wicking has occurred.

Also provided herein are methods of determining the levels of protective neutralizing antibodies induced by a SARS-CoV-2 vaccination or infection of a particular subject, comprising:

obtaining a test-specimen from a subject, wherein the subject was previously vaccinated; or known or suspected to have been previously infected with SARS-CoV-2; and detecting the presence and/or quantity of NAb according to methods provided herein for detection of neutralizing antibodies to SARS-CoV-2 in a test-specimen.

In certain embodiments, the subject was vaccinated or infected prior to obtaining the test-specimen in the range of: 1-365 days, 2-300 days, 3-275 days, 4-250 days, 5-225 days, 6-200 days, 7-180 days, 8-180 days, 9-180 days, 10-180 days, 11-180 days, 12-180 days, 13-180 days, and/or 14-180 days. In typical embodiments, detecting the presence of NAbs above a threshold value indicates protective antibody-based vaccination or infection.

Also provided herein are methods of identifying high-titer anti-SARS-CoV-2 NAbs samples induced by SARS-CoV-2 vaccination or infection of a particular subject, comprising:

obtaining a test-specimen from a subject, wherein the subject was previously vaccinated; or known or suspected to have been previously infected with SARS-CoV-2; and detecting the presence and/or quantity of NAb according to methods provided herein for detection of neutralizing antibodies to SARS-CoV-2 in a test-specimen.

Also provided herein are methods of measuring neutralizing antibody levels to SARS-CoV-2 in a specimen using an electronic device, said method comprising:

scanning a code into the electronic device that identifies a test to be performed and a particular specimen to be tested;

conduct the method of detecting the presence and/or quantity of NAb according to methods provided herein for detection of neutralizing antibodies to SARS-CoV-2 in a test-specimen; and scanning the results obtained from the test-cassette into the electronic device.

In typical embodiments, the results are processed directly on the electronic device. In particular embodiments the electronic device is a smartphone, tablet or personal computer. In other embodiments, the electronic device further connects to a database, thereby transferring the results to said database. In certain embodiments, the device connects to the database via email, WiFi, SMS, worldwide web, 4G, 5G, Bluetooth and/or USB.

In certain embodiments of the inventive method, the test results are scanned into an electronic device. The electric device can be a fixed computing device and/or a mobile computing device. The electric device can be at least one of a desktop personal computer, laptop or notebook personal computer, tablet computer, personal digital assistant, smartphone, smartwatch, smartcard, bracelet, smart clothing item, smart jewelry, media internet device, head-mounted display, or wearable glasses.

In other embodiments, the electronic device may include an operating system (OS) serving as an interface between hardware and/or physical resources of the electronic device and a user. The electronic device may include one or more processors, memory devices, network devices, drivers, or the like, as well as input/output (I/O) sources, such as touchscreens, touch panels, touch pads, virtual or regular keyboards, virtual or regular mice, and the like.

In particular embodiments, the electronic device into which the test results are scanned may be in communication with another electronic device, serving as a central computer or server computer, over one or more networks, such as a Cloud network, the Internet, intranet, Internet of Things ("IoT"), proximity network, wireless/cellular communication network (such as 3G, 4G, 5G, and/or 6G), Bluetooth, etc. Further, the electronic device into which the test results are scanned and/or the central or server computer may be in communication with one or more third-party electronic devices over the one or more networks. The central computer or server computer can be used to store, organize, keep track of, and/or analyze the test results scanned into multiple electronic devices. The third-party electronic devices can be used to access the data regarding the test results from the central computer or server computer, and/or to further analyze or utilize such data.

In other embodiments of the inventive method, the electronic device may transfer the test results to a database. The database may be contained in a central computer or server computer, or distributed across multiple electronic devices. To transfer test results, the electronic device may connect to the database via WiFi, WiMax, SMS, the Internet (including worldwide web), intranet, Internet of Things ("IoT"), proximity network, wireless/cellular communication network (such as 3G, 4G, 5G, and/or 6G), Cloud network, Bluetooth and/or USB (such as USB-A, USB-B, and/or USB-C). Results can also be downloaded from the electronic device for transfer to the database via storage media such as a USB flash drive, flash memory card, or SD memory card. The database may store and maintain any amount and type of data including but not limited to the presence or absence of SARS-CoV-2 neutralizing antibodies, relative level of SARS-CoV-2 neutralizing antibodies, presence or absence of red control line, green color intensity for the Test line (including that expressed as density units), red color intensity for the control line (including that expressed as density units), interpretations of the test results, estimated antibody titers, sample metadata, and/or other sample data such as patient demographic or genomic data, or patient vaccination and/or SARS-CoV-2 infection data.

Device Description and Test Principle

Also provided herein are SARS-CoV-2 test-cassette devices, comprising a sample pad, a conjugate pad, a nitrocellulose membrane and an absorbent pad, wherein the sample pad and/or conjugate pad comprises ACE2 or a functional fragment thereof, and wherein the conjugate pad comprises a viral-ACE2-binding protein coupled to a label. In certain embodiments, the ACE2 is bound directly on the sample pad and/or conjugate pad; or ACE2 is bound to the sample pad and/or conjugate pad via a tag/anti-tag pair. In particular embodiments, ACE2 is bound to biotin; and the nitrocellulose membrane is bound to streptavidin. In particular embodiments, the viral-ACE2-binding protein is an RBD. In yet other embodiments, the conjugate pad further comprises a mixture of RBD coupled to a nanoparticle and control-antibody coupled to a nanoparticle. In other embodiments, the RBD is coupled to a gold nanoshell (GNS) and the control-antibody is a monoclonal antibody coupled to a gold nanosphere (GNP).

In particular embodiments, a whole-blood filter is present in lieu of the sample pad. In certain embodiments, the conjugate pad comprises a viral-ACE2-binding protein coupled to a label; and further comprises ACE2 or a functional fragment thereof. In particular embodiments, the ACE2 or functional fragment thereof is spatially separated from the viral-ACE2-binding protein. In one embodiment, the viral-ACE2-binding protein is an RBD region of a SARS-CoV-2 spike protein.

Also provided herein are SARS-CoV-2 test-cassette devices, comprising a whole blood filter, a conjugate pad, a nitrocellulose membrane and an absorbent pad, wherein the conjugate pad comprises ACE2 or a functional fragment thereof, and a viral-ACE2-binding protein coupled to a label. In certain embodiments, ACE2 is bound directly on the conjugate pad; or ACE2 is bound to the conjugate pad via a tag/anti-tag pair. In other embodiments, ACE2 is bound to biotin; and the nitrocellulose membrane is bound to streptavidin. In a particular embodiment, the viral-ACE2-binding protein is an RBD. In certain embodiments, the conjugate pad further comprises a mixture of RBD coupled to a nanoparticle and control-antibody coupled to a nanoparticle. In yet further embodiments, the RBD is coupled to a gold nanoshell (GNS) and the control-antibody is a monoclonal antibody coupled to a gold nanosphere (GNP). In yet other embodiments, the ACE2 or functional fragment thereof is spatially separated from the viral-ACE2-binding protein. In one embodiment, the viral-ACE2-binding protein is an RBD region of a SARS-CoV-2 spike protein.

As set forth herein, embodiments of the present invention include lateral flow detection test-cassette devices and systems for detecting and/or quantifying a particular target analyte based on detecting complex formation of the analyte (e.g., anti-RBD NAbs) with a known receptor (e.g., RBD).

In other embodiments, lateral flow assay systems, test-cassette devices and methods of the present invention, include an analytical membrane that is divided into one or more detection regions and one or more control regions. The detection region or regions can include a target analyte binding agent immobilized to a portion of the detection region such that it is not displaced when facilitating lateral flow across the analytical membrane. Lateral flow assay systems of the present invention can also include a conjugate pad within which a target analyte binding agent is contained. In some embodiments, a target analyte binding agent is contained within the conjugate pad but flows from the conjugate pad and across the analytical membrane towards the detection and control regions when lateral flow occurs. Lateral flow assay systems of the present disclosure can also include a sample pad that is positioned at one distal end of the lateral flow assay system (e.g., opposite an absorbent pad; see FIG. 13). A sample that contains (or may contain) a target analyte (e.g., anti-RBD NAbs) is applied to the sample pad. In some embodiments, a lateral flow assay system also comprises a wicking pad at an end of the device distal to the sample pad. The wicking pad generates capillary flow of the sample from the sample pad through the conjugate pad, analytical membrane, detection region, and control region.

In accordance with these embodiments, upon addition of a test-specimen to the sample pad, the facilitation of lateral flow causes a target-analyte within the sample to contact a first target analyte binding agent within the conjugate pad; subsequently, lateral flow causes the target analyte and the first target analyte binding agent to contact a second target analyte binding agent immobilized to a detection region of the analytical membrane. The presence and/or quantity of the target analyte is then determined based on detection of the analyte in the detection region also referred to herein as a "test-line" and/or in comparison to the control.

Product Overview/Test Principle:

In a particular embodiment, the invention IMMUNOPASS diagnostic assay is designed to measure relative levels of antibodies that block SARS-CoV-2 Spike protein Receptor Binding Domain (RBD) from binding to Angiotensin Converting Enzyme 2 (ACE2). The test lateral flow assay (LFA) that can be read after the test is properly completed by comparing the Test line intensity on the strip to reference standard (e.g., an "intensity scorecard" and the like) provided with each kit. Each lot of lateral flow strips is calibrated against an intensity card with lines labeled as "strong neutralizing", "moderate neutralizing" and "low/non-neutralizing" ranges. In another embodiment, the range of pre-determined values corresponds to High (H), Moderate-High (MH), Moderate to Moderate-High (M-MH), Moderate (M), Moderate to Not Detectable (M-ND) and Not Detectable (ND).

In these embodiments, plasma or serum separated from whole blood by standard procedures may be used in the assay. In another embodiment, a whole blood filter may be used on the test-cassette to separate the plasma or serum.

In a particular embodiment, the invention IMMUNOPASS test uses the following components:

1. Recombinant RBD from SARS-CoV-2 spike protein coupled to deep green Gold Nanoshells (GNS).
2. ACE2 fused to a tag protein (e.g., biotin).
3. A ligand (e.g., Mouse IgG monoclonal antibody) coupled to red Gold Nanospheres (GNP),
4. LFA strip striped with a tag binding protein (e.g., polystreptavidin) for the test and a receptor for the ligand coupled to GNP for the control lines.
5. Sterile 10 ul disposable pipette
6. Chase buffer consisting of proteins and detergents, stabilized by biocide.

Description of Exemplary Embodiment of Test Steps:

1. Open the IMMUNOPASS Test Kit containing all necessary materials to run the test, check for contents, and read the enclosed step-by-step instructions.
2. Dilute included lyophilized controls with 100 ul deionized water (not supplied).
3. Open the pouch containing a test cassette. All required reagents are already pre-dried on the cassette strip per description below.
4. Pipette 10 microliters of the 3 reconstituted controls with the included 10 uL micropipette and apply directly into the clearly marked sample port, one control per cassette.
5. After the controls are absorbed into the sample pad, immediately add 2-3 drops (~50 uL) of chase buffer to the same sample port.
6. After 10 minutes compare test results obtained with the 3 control strips (high, medium and low) to the included scorecard.
7. If scorecard line intensities match the test lines obtained with control strips in the cassettes, proceed with measuring individual plasma or serum samples using the same procedure as outlined in steps (4)-(6), using sample plasma or serum.
8. After 10 minutes, interpret results with the included scorecard.

Control Material In certain embodiments, the controls are prepared by lyophilizing SAD-S35 neutralizing antibody (ACRO Biosystems) at a commercial GMP certified facility (Argonaut, Carlsbad, Calif.). The control antibodies used herein can be obtained from any patient previously infected with SARS-CoV-2. In this embodiment, the control antibody was derived from a SARS-CoV-2 infected patient and is recombinantly produced from human 293 cells (HEK293). The antibody recognizes the SARS-CoV-2 Spike Protein RBD domain and inhibits interaction between SARS-CoV-2 RBD and ACE2 with IC50 of 1.5 ug/mL. In one embodiment provided herein, the controls that are provided with the test kit include:

1. Internal Control—The control line should change from no line to red line on each strip for every test and checks that flow of reagents is satisfactory.
2. Three Neutralizing antibody Controls:
    (a) High level of lyophilized neutralizing anti-SARS-CoV-2 IgG1 resuspended with one vial of negative serum as described in the Instructions for Use.
    (b) Moderate level of lyophilized neutralizing anti-SARS-CoV-2 IgG1 resuspended with one vial of negative serum as described in the Instructions for Use.
    (c) Low level of lyophilized neutralizing anti-SARS-CoV-2 IgG1 resuspended with one vial of negative serum as described in the Instructions for Use.
3. Negative Control: Lyophilized negative human serum resuspended as described in Instructions for Use.

In this embodiment, the controls will be used only once upon reconstitution.

Interpretation of Results

In particular embodiments, assessment of invention IMMUNOPASS test results is performed after the 3 positive and negative controls have been examined and determined to be valid. If the controls are not valid, the patient results should not be interpreted.

Levels of neutralizing antibodies are interpreted by comparing the intensity of the Test line in the cassette with the supplied scorecard that is color-matched to actual test lines (see FIG. 2 where the control line is red). In typical embodiments, users will have an option to run three provided controls (high, moderate and low) to confirm their results observed using patient plasma or serum. The interpretation of the results will be done as follows. Application of 10 ul "high neutralizing" control results in a light/'ghost' line with a low intensity. Application of 10 ul of "moderate neutralizing" control results in a line with a moderate intensity. Application of 10 ul of "non-neutralizing" control results in a line with a high intensity. Plasma or serum samples falling within ranges of high, moderate and low/non-neutralizing are reported as such. Repeat testing should be performed if the control line does not develop. Repeat testing should also be performed if the user is unsure he/she performed the test according to the instructions.

FIG. 2 shows one embodiment of an IMMUNOPASS Scorecard for measuring relative levels of neutralizing antibodies in plasma or serum. Statistical analysis indicates that density units below 183,197 correlates with VSV pseudotype neutralizing antibody titers of ≥1:320 and result in no line or a 'ghost' line. Density units of samples between 183,197 and 421,750 correlates with pseudotype titers >1:80 but <1:320 and result in a moderately weak line. Density units from samples with titers higher than 421,750 correlates with low or non-neutralizing plasma/serum and result in a strong line. Density units for the image in FIG. 2 show high, moderate and low/none as 91,496, 311,536, and 923,965, respectively.

TABLE 1

Interpretation of Results

| | C Line | Neutralization Lines | Test Result Interpretation |
|---|---|---|---|
| 1 | not present | Any | Invalid Test. The specimen must be retested with another cassette |
| 2 | + | No or very faint line | Valid Test, High levels of neutralizing antibodies present Compare to scorecard. |
| 3 | + | Moderately positive Line | Valid Test, Moderate levels of neutralizing antibodies present. Compare scorecard |
| 4 | + | Strongly, postive line | Valid Test, Low level or non-neutralizing antibodies present. Compare to scorecard |

The invention IMMUNOPASS Test strip is a lateral flow assay strip comprising (a) sample pad (b) conjugate pad (c) nitrocellulose membrane and (d) absorbent pad. In one embodiment, for the IMMUNOPASS diagnostic test, we employ the following reagent configuration. The sample pad is infused with ACE2-tag (e.g., biotin and the like), while conjugate pad is infused with a mixture of RBD coupled to GNS and a mouse monoclonal antibody coupled to GNP as a constant assay control. The purpose of the control bead is to provide reassurances regarding sample addition, reconstitution, and flow. If control line cannot be visualized with the human eye, the test is considered invalid.

To perform the test, 6.8 microliters (ul) of plasma or serum or 10 ul of whole blood are applied to the sample pad in the sample port and immediately followed by three drops (~50 ul) of chase buffer. The plasma/serum+chase buffer reconstitutes ACE2 reagent dried in sample pad that then mixes with sample and flows towards the RBD-GNS+Mouse Mab-GNP dried on conjugate pad. Upon flowing through the RBD-GNS the neutralizing antibody (NAb), if present, competes with ACE2-tag for binding to the RBD-GNS. The more NAb is present in a sample, the less ACE2-tag can bind to the RBD. The reaction mixture is drawn by capillary action towards two zones striped onto nitrocellulose membrane, separated by ~5 mm. First is the polystreptavidin (test) zone that rapidly captures any RBD-GNS-ACE2-tag complex. The more ACE2-tag is bound to the bead, the stronger the signal. In this competitive assay the stronger the signal, the less NAb is present in a sample. Hence, the assay provides a reverse relation between test zone intensity and the amount of analyte (NAb) in a sample.

Figure 3A:
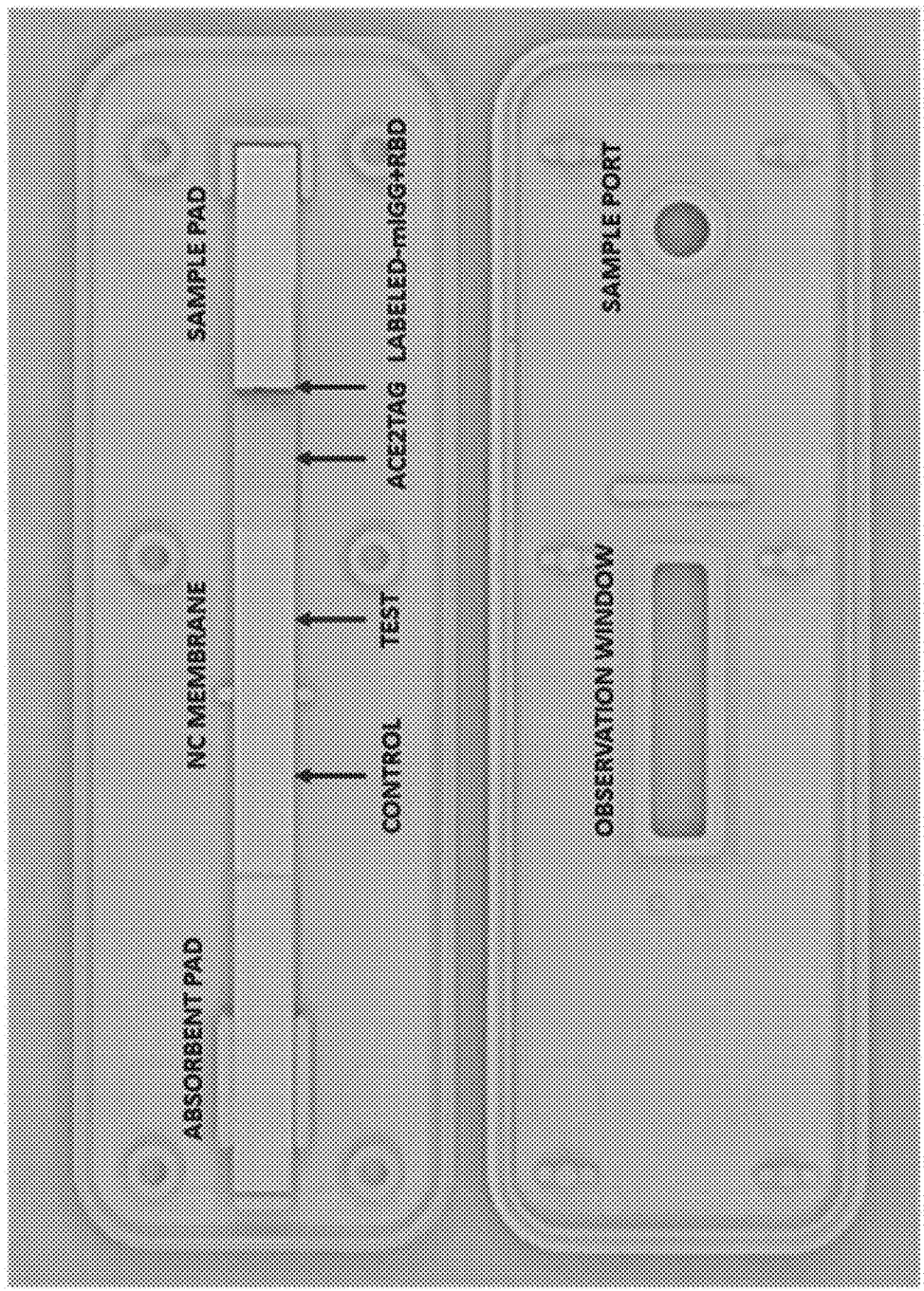
FIG. 3B corresponds to the internal placement of particular components of a particular embodiment of an IMMUNOPASS lateral flow strip cassette.
Figure 3B:
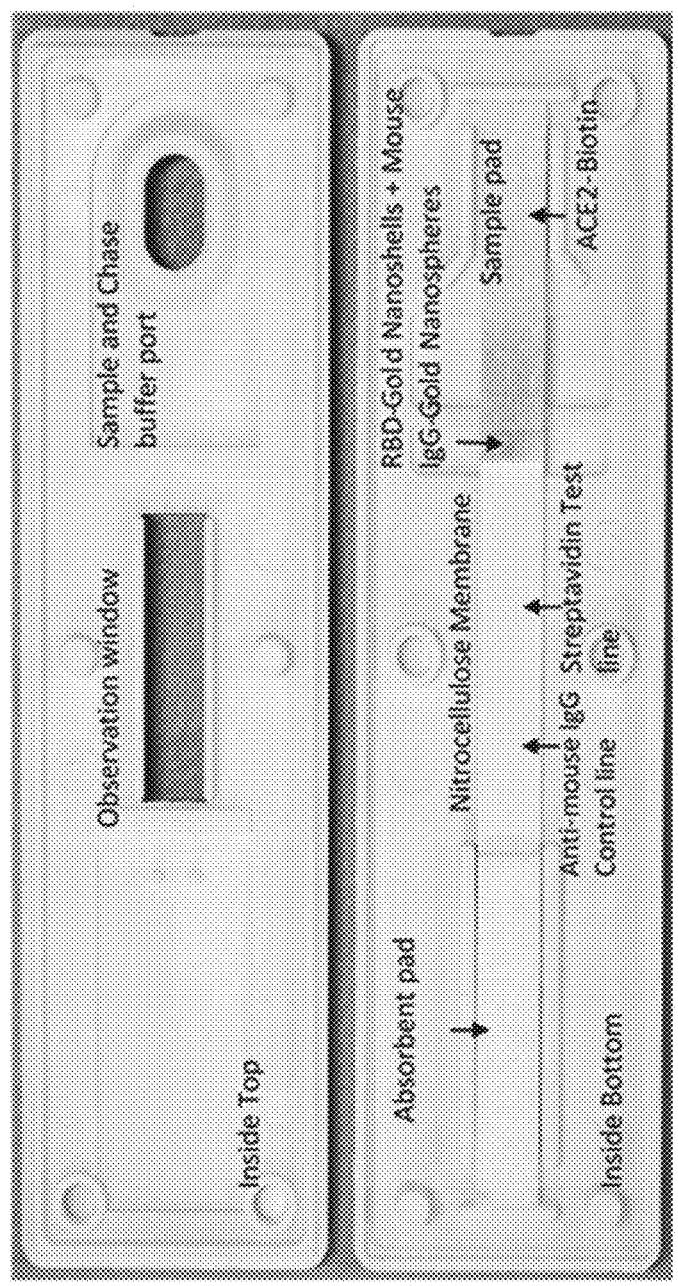

FIG. 3 corresponds to the internal placement of components of an IMMUNOPASS lateral flow strip cassette. Liquid flows from right to left in the figure. Mixture of RBD-GNS+Mouse mAb-GNS are deposited onto the conjugate pad area as can be observed by a gray blush on the pad. ACE2-tag (e.g., ACE2-biotin and the like) is deposited on the sample pad directly under the sample port as indicated in the figure.

The invention IMMUNOPASS test was developed using recombinant RBD that was made at Sapphire Biotech and covalently coupled to Carboxyl Gold Nanoshells purchased from NanoComposix (San Diego, Calif.). ACE2 was also produced using recombinant methods and modified with a tag. Control mouse anti-QSOX1 monoclonal antibody was produced from mouse hybridomas in house and purified on a protein A/G column. It was covalently coupled to Carboxyl Gold Nanoshells purchased from NanocComposix (San Diego, Calif.) and serves as an assay control reacting with membrane striped donkey anti-mouse low cross-reactivity antibody purchased from Jackson Immunoresearch (West Grove, Pa.). The test capture zone consists of polystreptavidin-350 reagent and was obtained from BBI Solutions (Crumlin, UK). All materials used in IMMUNOPASS come with certificates of analysis.

In typical embodiments, IMMUNOPASS uses a lateral flow assay platform where each sample is run individually. However, in other embodiments, one operator can comfortably run batches of 10 cassettes. Since the total time required to perform the test is ~10 minutes, throughput is ~60 cassettes per hour.

Cross-Reactivity:

We used 75 samples collected pre-December 2019 from patients with respiratory infections, an ideal control for this test (see Table 2 below). In Applicant Table 2, serum samples collected prior to December 2019 do not block RBD from binding to ACE2 and therefore do not neutralize SARS-CoV-2. Sample IDs beginning with "S" represent serum collected from patients with respiratory infections. ND samples are normal donor plasma samples collected prior to December 2019.

TABLE 2

| Sample number | Sample ID | Density Units |
| --- | --- | --- |
| 1 | Pos Ctrl | 23380 |
| 2 | Neg Ctrl | 1002112 |
| 3 | S316 | 624013 |
| 4 | S323 | 854562 |
| 5 | S360 | 600300 |
| 6 | S396 | 607203 |
| 7 | S397 | 887517 |
| 8 | S399 | 586898 |
| 9 | S406 | 788353 |
| 10 | S407 | 879791 |
| 11 | S408 | 851131 |
| 12 | S409 | 819735 |
| 13 | S410 | 665306 |
| 14 | S411 | 695303 |
| 15 | S415 | 965198 |
| 16 | S416 | 863744 |
| 17 | S417 | 754461 |
| 18 | S418 | 609052 |
| 19 | S434 | 1075630 |
| 20 | S440 | 688672 |
| 21 | S443 | 795873 |
| 22 | S444 | 857117 |
| 23 | S445 | 768170 |
| 24 | S455 | 734026 |
| 25 | S458 | 716446 |
| 26 | S461 | 588757 |
| 27 | S462 | 385243 |
| 28 | S463 | 836070 |
| 29 | S464 | 831254 |
| 30 | S489 | 638529 |
| 31 | S491 | 587518 |
| 32 | S493 | 414976 |
| 33 | S497 | 867534 |
| 34 | S499 | 777651 |
| 35 | S500 | 352656 |
| 36 | S502 | 898755 |
| 37 | S504 | 859239 |
| 38 | S507 | 879226 |
| 39 | S511 | 831918 |
| 40 | S514 | 571099 |
| 41 | S516 | 837640 |
| 42 | S546 | 740496 |
| 43 | S548 | 623002 |
| 44 | S550 | 649654 |
| 45 | S554 | 627117 |
| 46 | S593 | 577393 |
| 47 | S595 | 724273 |
| 48 | S605 | 484137 |
| 49 | S607 | 844352 |
| 50 | S608 | 745960 |
| 51 | S609 | 431503 |
| 52 | S610 | 490727 |
| 53 | S614 | 540020 |
| 54 | S619 | 748846 |
| 55 | S625 | 748539 |
| 56 | S628 | 757553 |
| 57 | S631 | 779326 |
| 58 | S667 | 775890 |
| 59 | S673 | 537397 |
| 60 | S675 | 811676 |
| 61 | S676 | 887716 |
| 62 | S678 | 595307 |
| 63 | S687 | 703162 |
| 64 | S688 | 784519 |
| 65 | S691 | 890002 |
| 66 | S694 | 707535 |
| 67 | S695 | 570580 |
| 68 | S696 | 849844 |
| 69 | S697 | 678786 |
| 70 | S698 | 695308 |
| 71 | ND93 | 598373 |
| 72 | ND100 | 763863 |
| 73 | ND108 | 758965 |
| 74 | ND111 | 733685 |
| 75 | ND130 | 661922 |
| 76 | ND134 | 647973 |
| 77 | ND135 | 713648 |

Figure 4A:
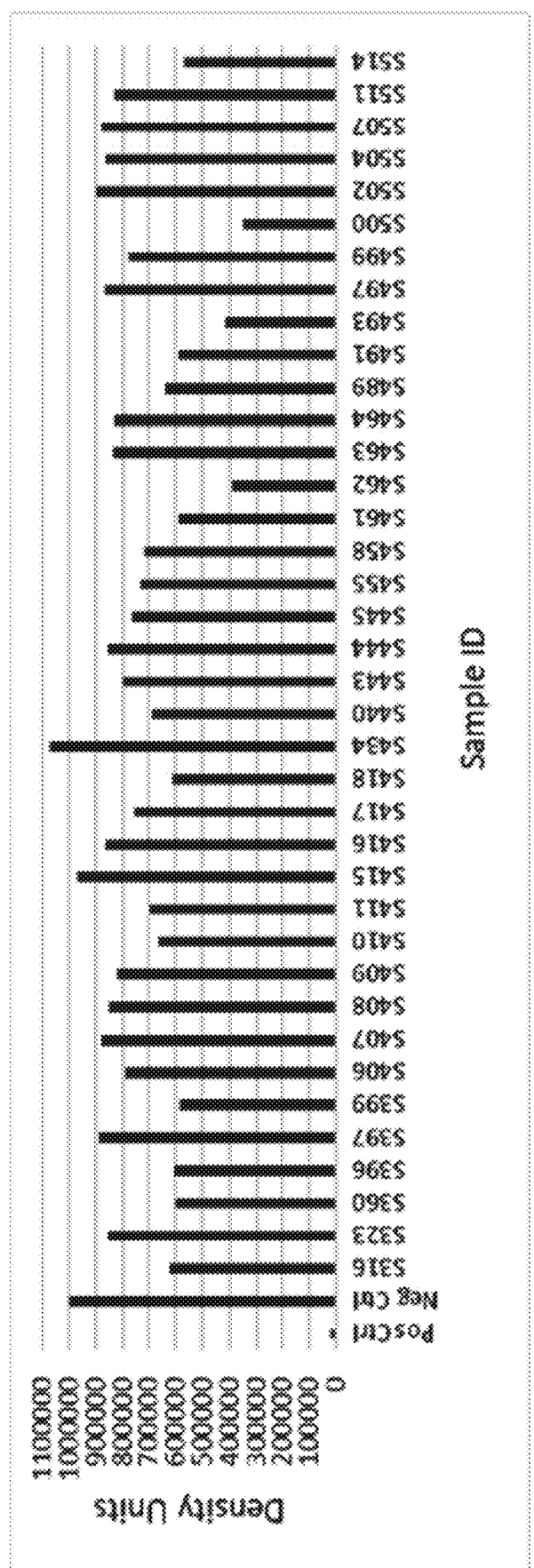
FIG. 4A shows a graphical representation of Applicant Table 1.
Figure 4B:
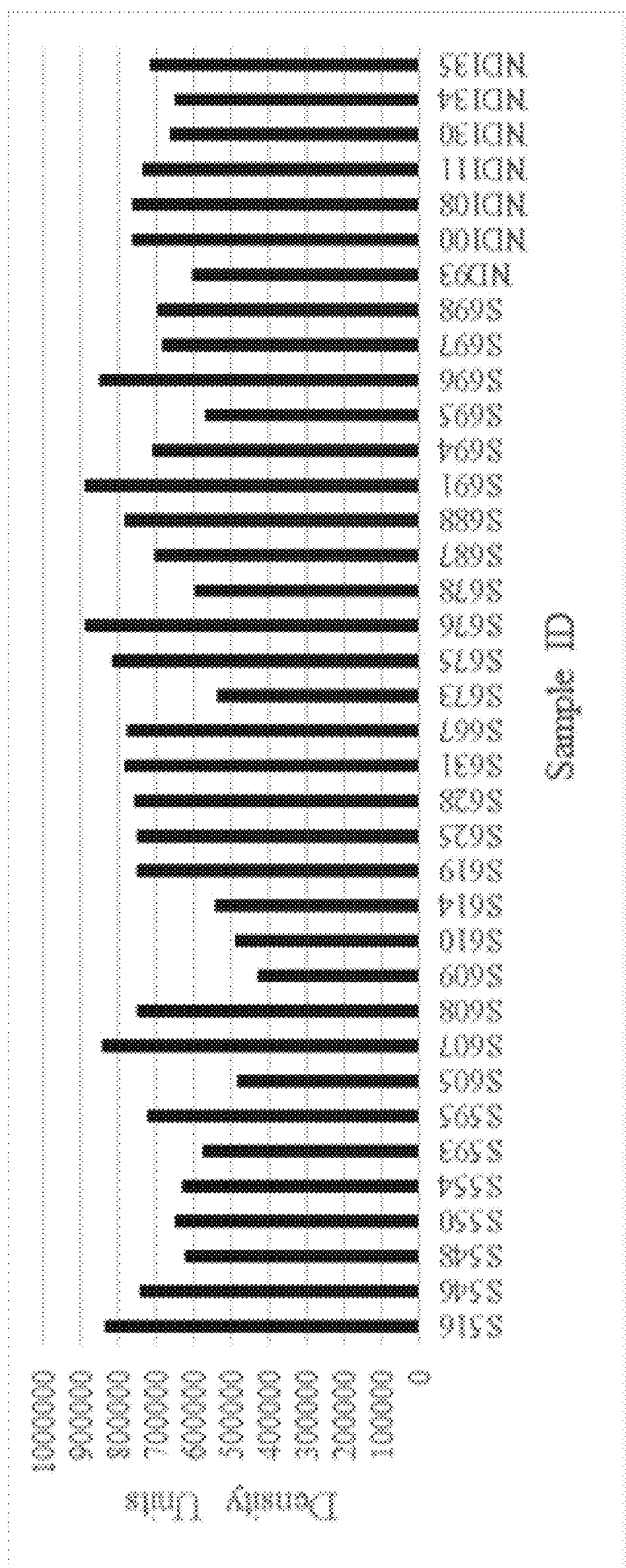
FIG. 4B also shows a graphical representation of Applicant Table 1.

FIG. 4A and FIG. 4B show a graphical representation of Applicant Table 2. All density units are higher than a density unit of 421,750 (<1:80 titer) except for 5462, 5493 and S500 which are 385,243, 414,976 and 353,656 which would put them in the moderate category between 1:80 and 1:160. Threshold for high levels of neutralizing antibodies is ≤183,197. None of the pre-December 2019 samples can be categorized as neutralizing.

Samples from blood collected tubes or plasma collection bags in Acid Citrate Dextrose (ACD), lithium heparin, EDTA and no additive showed no difference in the performance of the IMMUNOPASS test. All samples used in this study were from convalescent patients who were PCR-negative after recovering from COVID19.

Previously collected plasma samples for which neutralization titers are known were provided by Mayo Clinic for this retrospective analysis. The IMMUNOPASS test was performed in a blinded manner. Values were recorded in a Lateral flow cassette reader (RDS2500, iDetekt Biomedical, Austin, Tex.), images of the lines were recorded and values compared to neutralizing antibody titers measured by a VSV spike pseudotype assay developed by Mayo Clinic as listed in the Table 3 below.

APPLICANT TABLE 3

Retrospectively collected samples with known titers in the VSV pseudotype assay developed by Mayo Clinic.

| Sample ID | Density Units | Pseudovirus Titer |
| --- | --- | --- |
| 1 | 307,794 | 1:80 |
| 2 | 465,722 | 1:80 |
| 3 | 327,732 | 1:80 |
| 4 | 527,365 | 1:80 |
| 5 | 375,123 | 1:80 |
| 6 | 321,849 | 1:80 |
| 7 | 482,349 | 1:80 |
| 8 | 248,287 | 1:80 |

APPLICANT TABLE 3-continued

Retrospectively collected samples with known titers in the VSV pseudotype assay developed by Mayo Clinic.

| Sample ID | Density Units | Pseudovirus Titer |
|---|---|---|
| 9 | 126,868 | 1:80 |
| 10 | 646,291 | 1:80 |
| 11 | 528,067 | 1:160 |
| 12 | 447,976 | 1:160 |
| 13 | 228,423 | 1:160 |
| 14 | 200,864 | 1:160 |
| 15 | 234,909 | 1:160 |
| 16 | 142,004 | 1:160 |
| 17 | 397,359 | 1:160 |
| 18 | 746,014 | 1:160 |
| 19 | 521,463 | 1:160 |
| 20 | 150,587 | 1:160 |
| 21 | 433,456 | 1:320 |
| 22 | 208,211 | 1:320 |
| 23 | 193,252 | 1:320 |
| 24 | 76,148 | 1:320 |
| 25 | 74,044 | 1:320 |
| 26 | 225,628 | 1:320 |
| 27 | 107,877 | 1:320 |
| 28 | 205,476 | 1:320 |
| 29 | 57,891 | 1:320 |
| 30 | 224,445 | 1:320 |
| 31 | 62,122 | 1:640 |
| 32 | 32,706 | 1:640 |
| 33 | 33,650 | 1:640 |
| 34 | 34,868 | 1:640 |
| 35 | 10,855 | 1:640 |
| 36 | 54,934 | 1:640 |
| 37 | 70,500 | 1:640 |
| 38 | 59,804 | 1:640 |
| 39 | 9,728 | 1:640 |
| 40 | 64,033 | 1:640 |
| 41 | 49,753 | 1:1280 |
| 42 | 43,842 | 1:1280 |
| 43 | 19,690 | 1:1280 |
| 44 | 15,418 | 1:1280 |
| 45 | 32,755 | 1:1280 |
| 46 | 21,862 | 1:1280 |
| 47 | 44,298 | 1:1280 |
| 48 | 109,255 | 1:1280 |
| 49 | 50,260 | 1:1280 |
| 50 | 104,415 | 1:1280 |
| 51 | 51,278 | 1:2560 |
| 52 | 32,214 | 1:2560 |
| 53 | 18,549 | 1:2560 |
| 54 | 9,696 | 1:2560 |
| 55 | 14,021 | 1:2560 |
| 56 | 18,423 | 1:2560 |
| 57 | 10,622 | 1:2560 |
| 58 | 26,215 | 1:2560 |
| 59 | 32,671 | 1:2560 |

FIG. 5 shows a bar graph with individual points from Table 3 depicted therein. Density units shown on the y-axis were read by an iDetekt RDS-2500 lateral flow cassette reader.

FIG. 6 shows box plots of LFA values by titer. IMMUNOPASS values were calculated using VUC as 93% accurate for samples having low/no neutralization (1:80 or less), 74% accurate for samples with moderate neutralization (between 1:80 and 1:320) and 97% accuracy for samples that strongly neutralize SARS-CoV-2. From FIG. 6 it is evident that Positive Percent Agreement for neutralizing samples is 96.8%; and Percent Negative Agreement for non-neutralizing samples is 99.1%

Matrix Equivalency

IMMUNOPASS was performed using plasma from blood collection tubes obtained from the same donors containing: i) heparin, Acid Citrate Dextrose (ACD) and EDTA. IMMUNOPASS was also performed using serum. No measurable differences were observed among the test results using different anti-coagulants or no anti-coagulant.

EXAMPLES

Example 1: IMMUNOPASS SASRS-Cov-2 Neutralizing Antibody Test

Special Instrument Requirements:

In particular embodiments, the IMMUNOPASS test is used with the materials provided in a kit form, including, in a particular embodiment:

28 test cassettes (25 test and 3 controls) encoded with a QR code containing lot number and calibration data. Each cassette is contained within its own a pouch;

Instructions with a Scorecard for which users can visually match Test line intensities from (recovered) patient plasma with intensities on the Scorecard;

Three lyophilized controls: High, Medium, and Low; each to be reconstituted with 100 uL deionized water;

A dropper bottle containing chase buffer, 5 m; and thirty plastic micropipettes, 10 uL maximum volume.

Intended Use

The invention IMMUNOPASS SARS-Cov-2 Neutralizing Antibody Rapid Test is a rapid lateral flow chromatographic immunoassay designed for the semiquantitative measurement of neutralizing antibody in human serum or plasma (sodium heparin, potassium EDTA and acid dextrose citrate).

The IMMUNOPASS SARS-Cov-2 Neutralizing Antibody Rapid Test is useful as an aid in classifying individuals with a neutralizing immune response to SARS-CoV-2. Currently, it is unknown for how long antibodies persist following infection, but neutralizing antibodies by definition are protective against infection.

The results provided herein are for the semi-quantitative measurement of antibodies that neutralize the infectivity of SARS CoV-2. Antibodies, including Neutralizing antibodies to SARS-CoV-2 are generally detectable in blood several days after initial infection, although the duration of time antibodies are present post-infection is not well characterized. Individuals may have detectable virus present for several weeks following seroconversion. It is likely, but not known, if neutralizing antibodies prevent transmission of infectious virus.

Storage and Stability

It is recommended to store the rapid tests at 4° C. The cassettes should remain in the pouch with silica packs until use. Do not freeze. Do not use beyond the expiration date.

Specimen Collection and Preparation

The invention IMMUNOPASS SARS-Cov-2 Neutralizing Antibody Rapid Test is performed using human serum or plasma. In particular embodiments, plasma is collected using a tube containing Heparin, EDTA and/or ACD anti-coagulants. In certain embodiments, the serum or plasma is separated from blood as soon as possible to avoid hemolysis. Use only clear, non-hemolyzed specimens.

Testing should be performed immediately after specimen collection unless immediately frozen below −20° C. Do not leave the specimens at room temperature for longer than 3 days. Serum and plasma specimens may be stored at 2-8° C. for up to 3 days. For long-term storage, specimens should be kept below −20° C.

Bring specimens to room temperature prior to testing. Frozen specimens must be completely thawed and mixed well prior to testing. Specimens should not be frozen and thawed more than once.

If specimens are to be shipped, they should be packed in compliance with federal regulations for transportation of etiologic agents.

Materials

Materials Provided

| Kit components | Amount per Kit |
|---|---|
| Test cassettes | 28 individually wrapped |
| Chase buffer | 1 × 5 mL dropper botte |
| Negative neutralizing control | 1 × 200 uL vial |
| Medium neutralizing control | 1 × 200 uL vial |
| High neutralizing control | 1 × 200 uL vial |
| Capillaries, 10 uL fixed volume | 30/bag |
| Package Insert w/score card | 1 Package insert |

Additional Materials Required
Deionized Water for Reconstitution of Controls and Timer
Directions for Use Allow the test cassette, specimen, buffer, and/or controls to reach room temperature (15-30° C.) prior to testing.

1. Bring the pouch to room temperature before opening. Remove test cassettes from the sealed pouch and use within one hour.

2. Place the test cassette on a clean and level surface.

For Plasma Specimens:

To use the capillary pipets: Hold the capillary vertically and insert the tip into specimen without pressing the bulb, let the specimen travel to the Fill Line. (approximately 10 µl), and transfer the specimen to the sample well (S) of the test cassette by pressing the bulb, then add 3 drops of buffer (approximately 50 µl) to the sample well (S) and start the timer.

Figure 7:
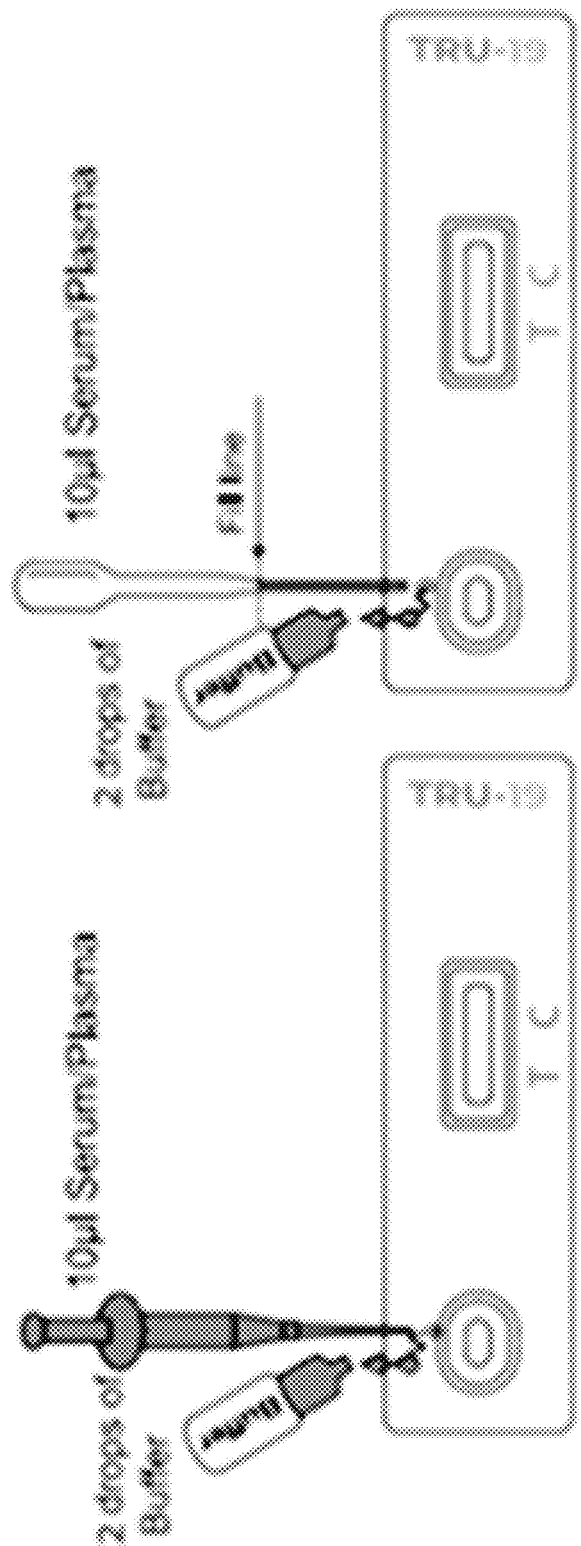
FIG. 7 shows a depiction of pipetting plasma to the sample along with buffer.
Figure 9A:
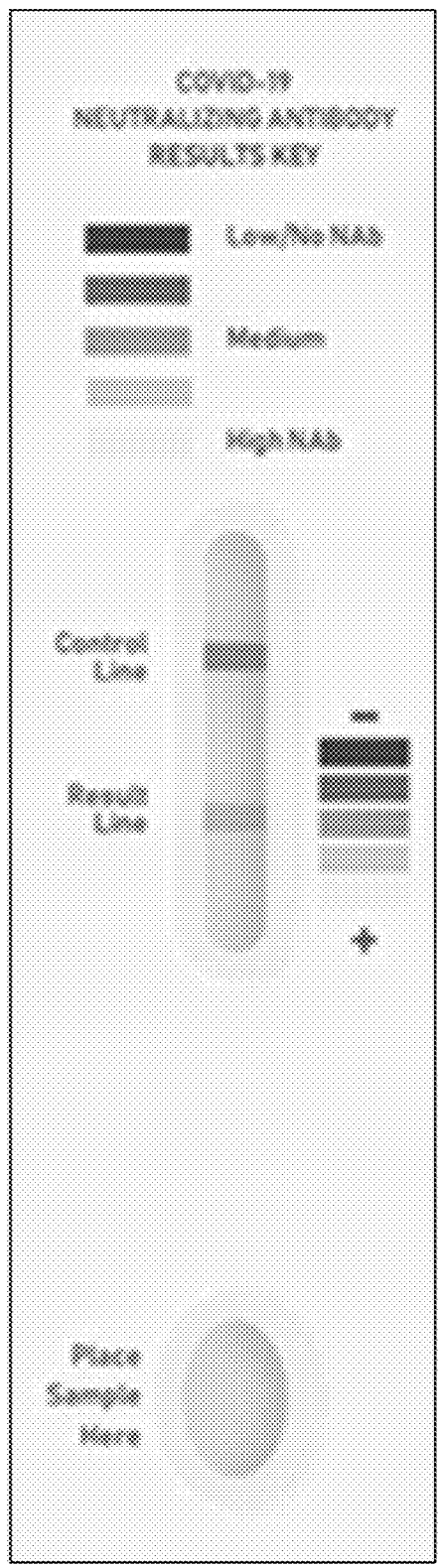
FIG. 9A shows a printed score card next to the observation window of an invention diagnostic cartridge.
Figure 9B:
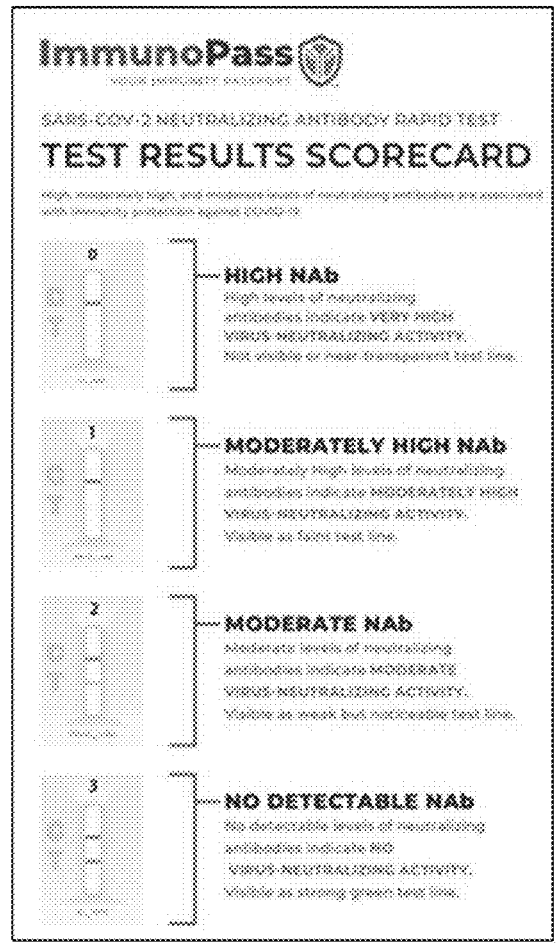
FIG. 9B shows a printed test-results score card for assessing 4 relative levels of NAbs from an invention diagnostic cartridge.

To use a micropipette: Pipette and dispense 10 µl of specimen to the sample well (S) of the test cassette, then add 2-3 drops of buffer (approximately 50 µl) to the buffer well (S) and start the timer (see FIG. 7).

3. Wait for the colored line(s) to appear. The test result should be read at 10 minutes. Do not interpret the result after 20 minutes.

Interpretation of Results

A red control line ("C" in FIG. 8A) is included in each test strip to ensure that the test was performed properly. Absence of the control line after 10 minutes indicates an invalid result (FIG. 7B). The color intensity of the dark green line in the test (T) region (see FIG. 8A) will vary based on the concentration and potency of neutralizing antibodies present in the sample.

Each IMMUNOPASS SARS-Cov-2 Neutralizing Antibody Rapid Test has a printed score card next to the observation window as shown in the FIG. 9. No line or ghost line in FIG. 9 indicates high levels of neutralizing antibodies that correlate with those measured in VSV pseudotype neutralizing antibody assays as stronger neutralizing capacity than 1:320. A weak or moderate line similar to the scorecard would correspond to neutralizing activity less than 1:320 but more than 1:80. A dark line similar or darker than the scorecard for low/none indicates low (1:80) or no neutralizing antibodies in the plasma/serum sample.

Quality Control

An internal procedural control is included in the test. A colored line appearing in the control line region (C) is an internal valid procedural control confirming adequate membrane wicking.

Control standards are supplied with this kit; it is recommended that the three controls be tested as a good laboratory practice to confirm the test procedure and to verify proper test performance.

Limitations

An invention IMMUNOPASS SARS-Cov-2 Neutralizing Antibody Rapid Test is contemplated for in vitro diagnostic use only. The test should be used for the semi-quantitative detection of SARS-COV-2 neutralizing antibodies in serum or plasma specimens only.

The Assay Procedure and the Interpretation of Assay Result should be followed closely when testing for the presence of SARS-CoV-2 virus specific neutralizing antibodies in the serum or plasma from individual subjects. For optimal test performance, proper sample collection is critical. Failure to follow the procedure may give inaccurate results.

Reading test results earlier than 10 minutes after the addition of Buffer may yield erroneous results. Do not interpret the result after 20 minutes.

The IMMUNOPASS SARS-Cov-2 Neutralizing Antibody Rapid Test only indicate the presence of SARS-COV-2 neutralizing antibodies in the specimen and should not be used as the sole criteria for the diagnosis of SARS-COV-2 infection.

In the early onset of symptoms, anti-SARS-COV-2 neutralizing antibody concentrations may be below detectable levels.

Results from immunosuppressed patients should be interpreted with caution.

As with all diagnostic tests, results must be interpreted together with other clinical information available to the physician.

A negative result for a sample indicates absence of detectable anti-SARS-CoV-2 neutralizing antibodies. Negative results do not preclude SARS-CoV-2 infection and should not be used as the sole basis for patient management decisions.

False positive results for neutralizing antibodies may occur due to cross-reactivity from pre-existing antibodies or other unknown causes. Samples with positive results should be confirmed with alternative testing method(s) and clinical findings before a diagnostic determination is made. A negative result can occur if the quantity of the anti-SARS-CoV-2 neutralizing antibodies present in the specimen is below the detection limits of the assay, or the antibodies that are detected are not present during the stage of disease in which a sample is collected.

Some specimens containing unusually high titer of rheumatoid factor may affect expected results.

Results from neutralizing antibody testing should not be used as the sole basis to diagnose or exclude SARS-CoV-2 infection or to inform infection status.

Testing should be performed within one hour after opening the pouch at room temperature.

Performance Characteristics

Assay Clinical Performance

Figure 10:
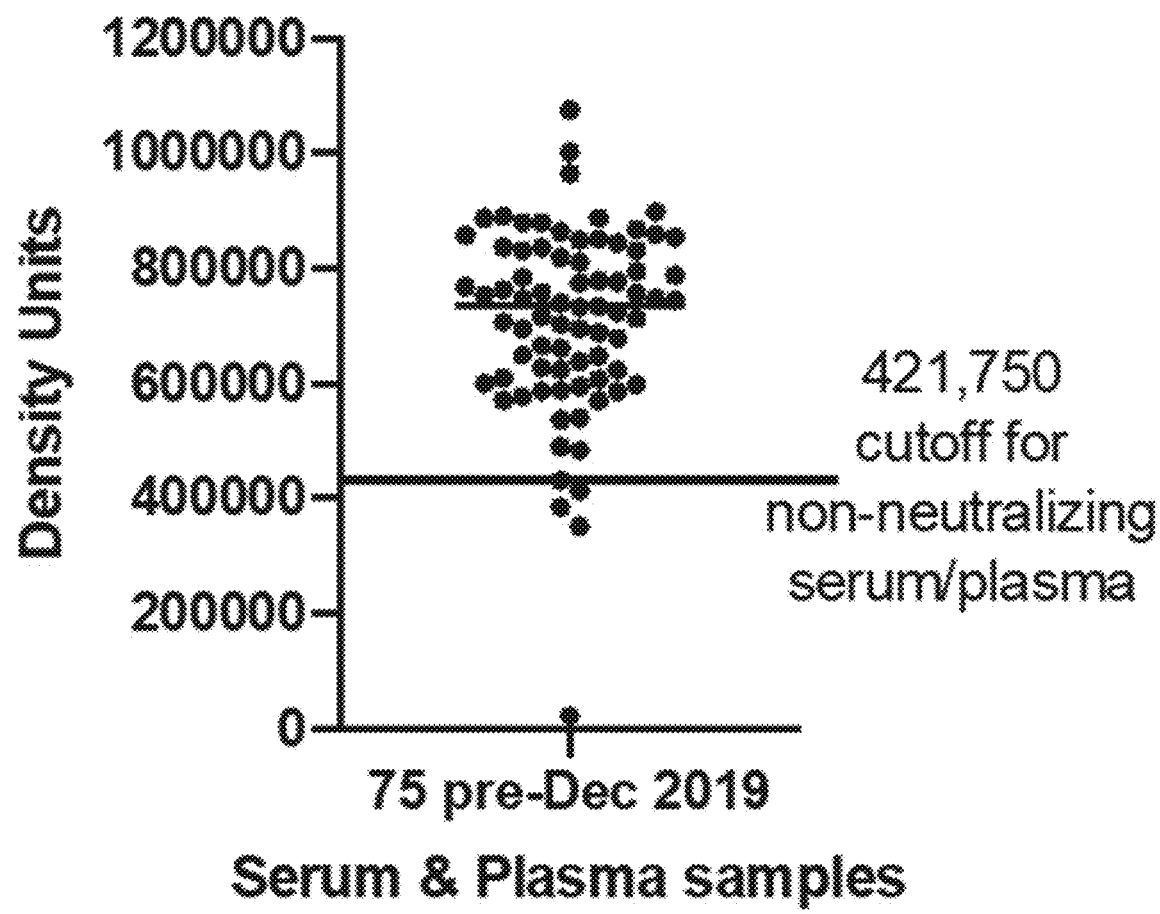
FIG. 10 shows the results of the clinical performance of the IMMUNOPASS SARS-Cov-2 Neutralizing Antibody Rapid Test (Serum/Plasma) evaluated by testing a total of 180 plasma (EDTA, ACD, heparin) clinical samples.
Figure 11:
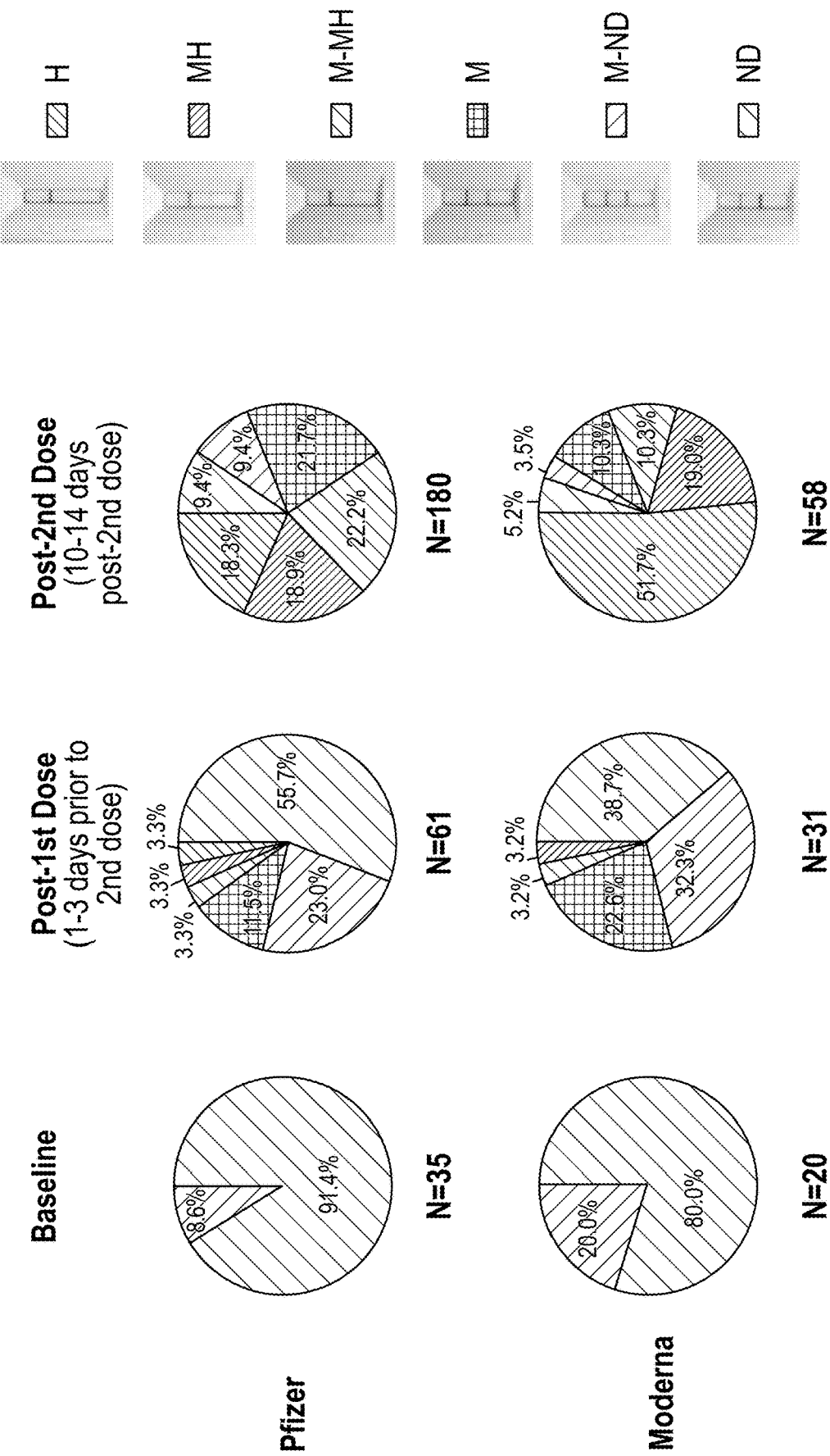
FIG. 11 shows the results from whole blood of evaluating vaccine-induced Nab levels.
Figure 12:
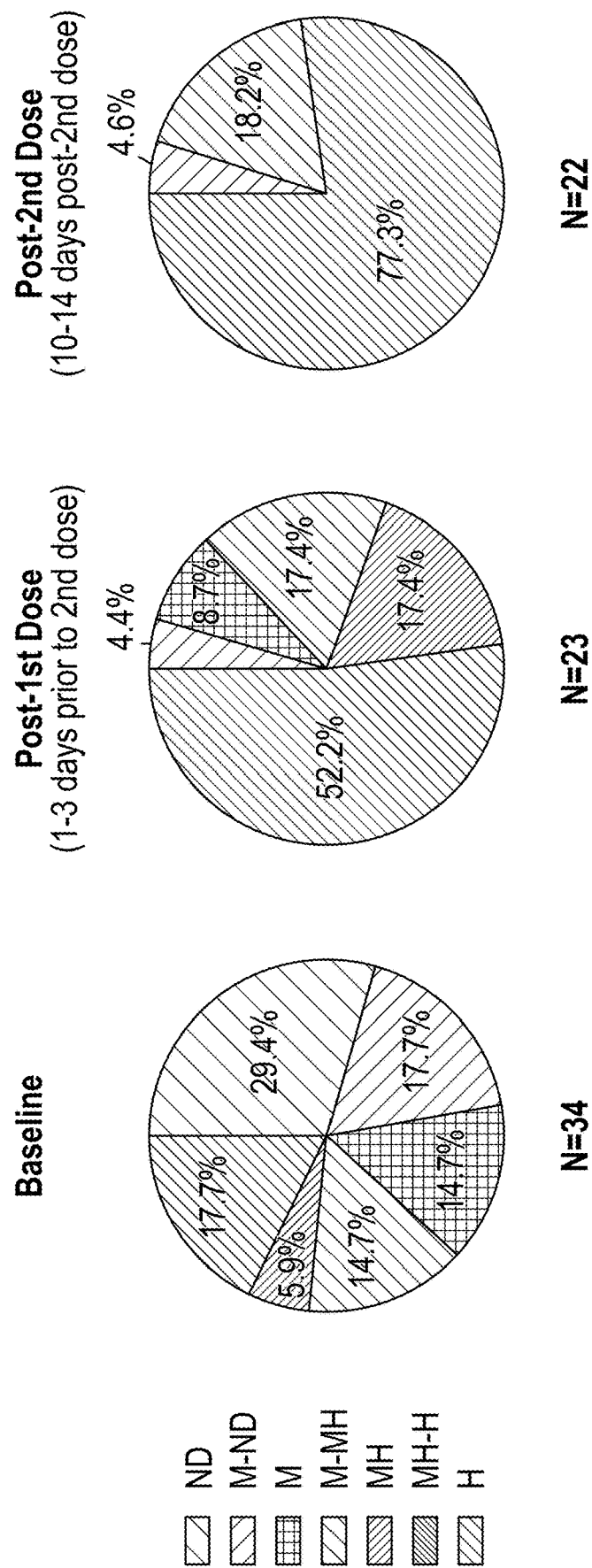
FIG. 12 shows the result from whole blood that previous natural infection with SARS-CoV-2 does not produce high levels of NAbs, whereas a single dose of vaccine in these previously SARS-CoV-2 infected subjects produces high levels of NAbs.

The clinical performance of the IMMUNOPASS SARS-Cov-2 Neutralizing Antibody Rapid Test (Serum/Plasma) was evaluated by testing a total of 180 plasma (EDTA, ACD, heparin) clinical samples—85 convalescent plasma samples with known neutralization titers by VSV Pseudovirus and 75 pre-December 2019 COVID-19 negative samples. The results are shown in FIG. 10.

Assay Cross Reactivity

Cross-reactivity of the IMMUNOPASS SARS-Cov-2 Neutralizing Antibody Rapid Test Cassette was evaluated using serum/plasma samples which contain antibodies to the pathogens listed below in Table 4. A total of 28 specimens from 12 different categories were tested. No false Positives were found in this set.

TABLE 4

| | |
|---|---|
| influenza A | NL63 (alpha coronavirus) |
| influenza B | OC43 (beta coronavirus) |
| Rhinovirus | HKU1 (beta coronavirus) |
| Parainfluenza | respiratory syncytial virus |
| Adenovirus | Coccidioidomycosis |
| 229E (alpha coronavirus) | |

Negative Agreement

Serum and plasma samples collected prior to December 2019 did not block RBD from binding to ACE2 and therefore did not neutralize SARS-CoV-2. The Negative Percent Agreement for non-neutralizing samples is 99.1%.

Positive Agreement

Figure 6:
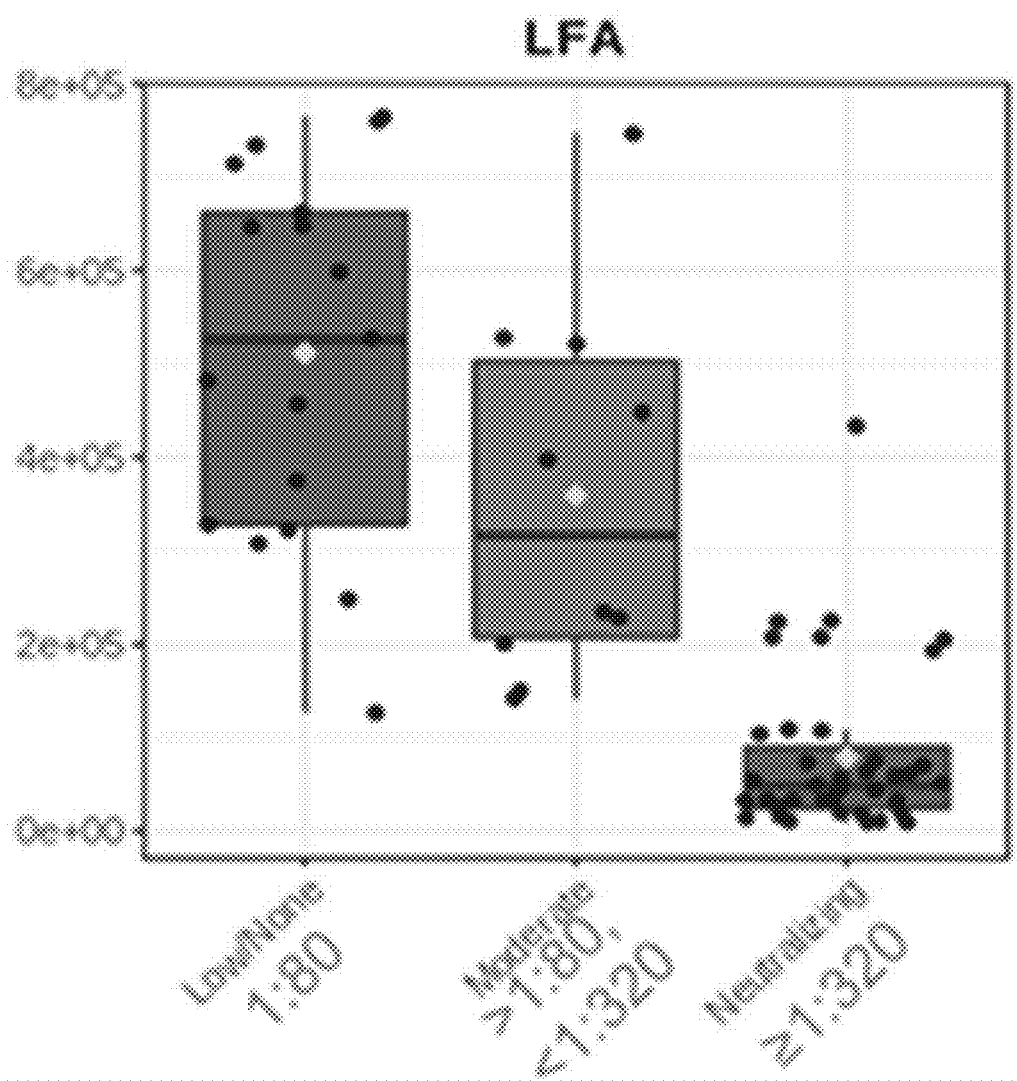
FIG. 6 shows box plots of LFA values by titer.

Box plots of LFA values by titer are shown in FIG. 6. Scores were calculated using VUC as 93% accurate for samples having low/no neutralization (1:80 or less), 74% accurate for samples with moderate neutralization (between 1:80 and 1:320) and 97% accuracy for samples that strongly neutralize SARS-CoV-2. Positive Percent Agreement for neutralizing samples is 96.8%.

Figure 5:
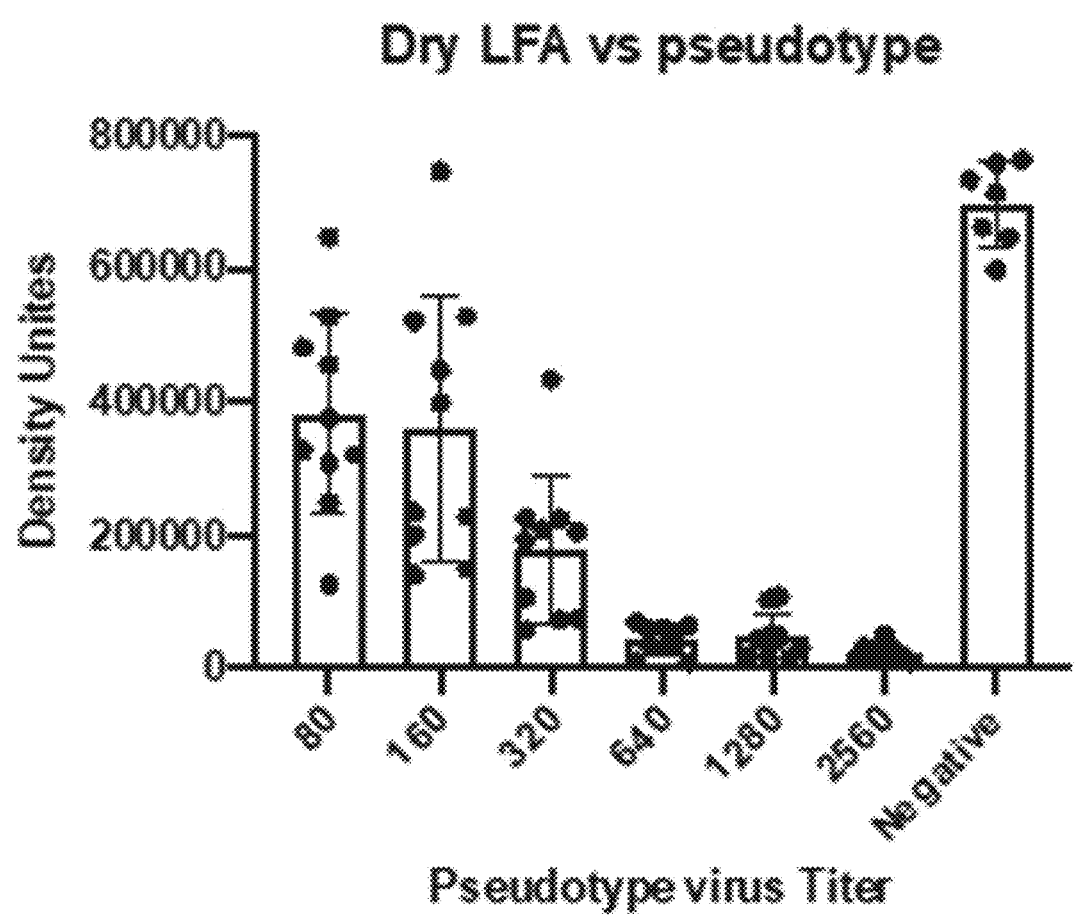
FIG. 5 shows a bar graph with individual points from Table 3 depicted therein.

FIG. 5 shows a Bar graph with individual points. Density units shown on the y-axis were read by an iDetekt RDS-2500 lateral flow cassette reader.

Class Specificity

IMMUNOPASS SARS-Cov-2 Neutralizing Antibody Rapid Test Cassette is agnostic to antibody isotype.

Plasma Specimens with Anticoagulants

IMMUNOPASS SARS-Cov-2 Neutralizing Antibody Rapid Test Cassette was tested using plasma from blood collection tubes obtained from the same donors containing: i) heparin, Acid Citrate Dextrose (ACD) and EDTA. The test was also performed using serum. No measurable differences were observed among the test results using different anticoagulants or no anti-coagulant.

This application includes a sequence listing submitted electronically, in a file entitled 127607-0006UT01_SL.txt, created on Jul. 19, 2021 and having a size of 9.79 kilobytes (KB), which is incorporated by reference herein.

The invention claimed is:

1. A method for detection and measurement of neutralizing antibody levels to SARS-COV-2 in a test-specimen, said method comprising:
obtaining a test-specimen from a subject;
transferring the test-specimen to a sample well of a test-cassette, wherein the cassette further comprises a sample pad, a conjugate pad, a nitrocellulose membrane and an absorbent pad, wherein the sample pad and/or conjugate pad comprises ACE2 or a functional fragment thereof prior to introduction of a sample, wherein the conjugate pad comprises a viral-ACE2-binding protein coupled to a label prior to introduction of a sample;
adding a buffer; and
reading the results from the test-cassette.

2. The method of claim 1, wherein the test-specimen is whole blood, plasma, serum or saliva.

3. The method of claim 1, wherein the whole blood, plasma, serum or saliva is obtained from a patient either known or suspected of recovering from COVID19 disease; or known to have been vaccinated for SARS-COV-2.

4. The method of claim 1, wherein ACE2 is bound directly on the sample pad, or ACE2 is bound to the sample pad via a tag/anti-tag pair.

5. The method of claim 4, wherein ACE2 is bound to biotin; and the nitrocellulose membrane is bound to streptavidin.

6. The method of claim 1, wherein the viral-ACE2-binding protein is an RBD.

7. The method of claim 2, wherein the plasma is obtained using an anticoagulant.

8. The method of claim 7, where in the anticoagulant is selected from the group consisting of: heparin, dipotassium EDTA or sodium citrate.

9. The method of claim 1, wherein the label is selected from a nanoparticle, bead, latex bead, aptamer, oligonucleotide and/or a quantum dot.

10. The method of claim 1, wherein the conjugate pad further comprises a mixture of RBD coupled to a nanoparticle and control-antibody coupled to a nanoparticle.

11. The method of claim 10, wherein the RBD is coupled to a gold nanoshell (GNS) and the control-antibody is a monoclonal antibody coupled to a gold nanosphere (GNP).

12. The method of claim 1, wherein reading the results from the test-cassette further comprises determining the intensity of a test-line in the test-cassette compared with a reference standard.

13. The method of claim 12, wherein the reference standard is a scorecard.

14. The method of claim 1, wherein the level of anti-SARS-COV-2 NAbs in the test-specimen is reported as falling within a range of pre-determined values.

15. The method of claim 14, wherein the range of pre-determined values corresponds to high, moderate or low/non-neutralizing relative to three respective controls.

16. The method of claim 14, wherein the range of pre-determined values corresponds to High (H), Moderate-High (MH), Moderate to Moderate-High (M-MH), Moderate (M), Moderate to Not Detectable (M-ND) and Not Detectable (ND).

17. A method of determining the levels of protective neutralizing antibodies induced by a SARS-COV-2 vaccination or infection of a particular subject, comprising:
a. obtaining a test-specimen from a subject, wherein the subject was previously vaccinated; or known or suspected to have been previously infected with SARS-CoV-2; and
b. detecting the presence and/or quantity of NAb according to claim 1.

18. The method of claim 17, wherein the subject was vaccinated or infected prior to obtaining the test-specimen in the range of: 1-365 days, 2-300 days, 3-275 days, 4-250 days, 5-225 days, 6-200 days, 7-180 days, 8-180 days, 9-180 days, 10-180 days, 11-180 days, 12-180 days, 13-180 days, and/or 14-180 days.

19. The method of claim 17, wherein detecting the presence of NAbs above a threshold value indicates protective antibody-based vaccination or infection.

20. A method of identifying high-titer anti-SARS-COV-2 NAbs samples induced by SARS-COV-2 vaccination or infection of a particular subject, comprising:
   a. obtaining a test-specimen from a subject, wherein the subject was previously vaccinated; or known or suspected to have been previously infected with SARS-CoV-2; and
   b. detecting the presence and/or quantity of NAb according to claim 1.

21. A method of measuring neutralizing antibody levels to SARS-COV-2 in a specimen using an electronic device, said method comprising:
   a. scanning a code into the electronic device that identifies a test to be performed and a particular specimen to be tested;
   b. conduct the method of claim 1; and
   c. scanning the results obtained from the test-cassette into the electronic device.

22. The method of claim 21, wherein the results are processed directly on the electronic device.

23. The method of claim 21, wherein the electronic device is a smartphone, tablet or personal computer.

24. The method of claim 21, wherein the electronic device further connects to a database, thereby transferring the results to said database.

25. The method of claim 21, wherein the device connects to the database via email, WiFi, SMS, worldwide web, 4G, 5G, Bluetooth and/or USB.

26. A SARS-COV-2 test-cassette device, comprising a sample pad, a conjugate pad, a nitrocellulose membrane and an absorbent pad, wherein the sample pad and/or conjugate pad comprises ACE2 or a functional fragment thereof prior to introduction of a sample, and wherein the conjugate pad comprises a viral-ACE2-binding protein coupled to a label prior to introduction of a sample.

27. The test-cassette of claim 26, wherein ACE2 is placed directly on the sample pad and/or conjugate pad; or ACE2 is placed on the sample pad and/or conjugate pad via a tag/anti-tag pair.

28. The test-cassette of claim 26, wherein ACE2 is bound to biotin; and the nitrocellulose membrane is bound to streptavidin.

29. The test-cassette of claim 26, wherein the viral-ACE2-binding protein is an RBD.

30. The test-cassette of claim 26, wherein the conjugate pad further comprises a mixture of RBD coupled to a nanoparticle and control-antibody coupled to a nanoparticle.

31. The test-cassette of claim 30, wherein the RBD is coupled to a gold nanoshell (GNS) and the control-antibody is a monoclonal antibody coupled to a gold nanosphere (GNP).

32. The test-cassette of claim 26, wherein a whole-blood filter is present.

33. The test-cassette of claim 32, wherein the conjugate pad comprises a viral-ACE2-binding protein coupled to a label and further comprises ACE2 or a functional fragment thereof.

34. The test-cassette of claim 33, wherein the ACE2 or functional fragment thereof is spatially separated from the viral-ACE2-binding protein.

35. The test-cassette of claim 26, wherein the viral-ACE2-binding protein is an RBD region of a SARS-COV-2 spike protein.

36. A SARS-COV-2 test-cassette device, comprising a whole blood filter, a conjugate pad, a nitrocellulose membrane and an absorbent pad, wherein the conjugate pad comprises ACE2 or a functional fragment thereof prior to introduction of a sample, and a viral-ACE2-binding protein coupled to a label prior to introduction of a sample.

37. The test-cassette of claim 36, wherein ACE2 is bound directly on the conjugate pad; or ACE2 is bound to the conjugate pad via a tag/anti-tag pair.

38. The test-cassette of claim 36, wherein ACE2 is bound to biotin, and the nitrocellulose membrane is bound to streptavidin.

39. The test-cassette of claim 36, wherein the viral-ACE2-binding protein is an RBD.

40. The test-cassette of claim 36, wherein the conjugate pad further comprises a mixture of RBD coupled to a nanoparticle and control-antibody coupled to a nanoparticle.

41. The test-cassette of claim 40, wherein the RBD is coupled to a gold nanoshell (GNS) and the control-antibody is a monoclonal antibody coupled to a gold nanosphere (GNP).

42. The test-cassette of claim 36, wherein the ACE2 or functional fragment thereof is spatially separated from the viral-ACE2-binding protein.

43. The test-cassette of claim 36, wherein the viral-ACE2-binding protein is an RBD region of a SARS-COV-2 spike protein.

44. A SARS-COV-2 test-cassette device, comprising a sample pad, a conjugate pad, a nitrocellulose membrane and an absorbent pad, wherein the sample pad and/or conjugate pad comprises ACE2 or a functional fragment thereof prior to introduction of a sample, and wherein the conjugate pad comprises a viral-ACE2-binding protein coupled to a label prior to introduction of a sample, wherein ACE2 or a functional fragment thereof is bound to biotin; and the nitrocellulose membrane is bound to streptavidin.

45. The test-cassette of claim 44, wherein ACE2 is bound directly on the sample pad and/or conjugate pad; or ACE2 is bound to the sample pad and/or conjugate pad via a tag/anti-tag pair.

46. The test-cassette of claim 44, wherein the viral-ACE2-binding protein is an RBD.

47. The test-cassette of claim 44, wherein the conjugate pad further comprises a mixture of RBD coupled to a nanoparticle and control-antibody coupled to a nanoparticle.

48. The test-cassette of claim 47, wherein the RBD is coupled to a gold nanoshell (GNS) and the control-antibody is a monoclonal antibody coupled to a gold nanosphere (GNP).

49. The test-cassette of claim 44, wherein a whole-blood filter is present in lieu of the sample pad.

50. The test-cassette of claim 49, wherein the conjugate pad comprises a viral-ACE2-binding protein coupled to a label; and further comprises ACE2 or a functional fragment thereof.

51. The test-cassette of claim 50, wherein the ACE2 or functional fragment thereof is spatially separated from the viral-ACE2-binding protein.

52. The test-cassette of claim 44, wherein the viral-ACE2-binding protein is an RBD region of a SARS-COV-2 spike protein.

53. A SARS-COV-2 test-cassette device, comprising a sample pad, a conjugate pad, a nitrocellulose membrane and an absorbent pad, wherein the sample pad and/or conjugate pad comprises ACE2 or a functional fragment thereof prior to introduction of a sample, and wherein the sample pad and/or conjugate pad comprises a viral-ACE2-binding protein coupled to a label, prior to introduction of a sample.

54. The test-cassette of claim 53, wherein ACE2 or a functional fragment thereof is bound to the nitrocellulose membrane.

* * * * *